United States Patent
Crane et al.

(12) 
(10) Patent No.: US 6,667,194 B1
(45) Date of Patent: Dec. 23, 2003

(54) METHOD OF BONDING DIE CHIP WITH UNDERFILL FLUXING COMPOSITION

(75) Inventors: Lawrence N. Crane, Brookfield, CT (US); Mark M. Konarski, Old Saybrook, CT (US); J. Paul Krug, Middletown, CT (US); Andrew D. Messana, Newington, CT (US); John G. Woods, Farmington, CT (US)

(73) Assignee: Henkel Loctite Corporation, Rocky Hill, CT (US)

( * ) Notice: Subject to any disclaimer, the term of this patent is extended or adjusted under 35 U.S.C. 154(b) by 15 days.

(21) Appl. No.: 10/082,278

(22) Filed: Feb. 26, 2002

Related U.S. Application Data

(63) Continuation of application No. PCT/US01/31020, filed on Oct. 4, 2001.
(60) Provisional application No. 60/328,055, filed on Oct. 9, 2001, and provisional application No. 60/237,541, filed on Oct. 4, 2000.

(51) Int. Cl.[7] ............................ C08L 63/02; H01L 21/56
(52) U.S. Cl. ........................ 438/127; 428/620; 525/485; 525/488; 525/523; 525/533
(58) Field of Search ........................ 438/127; 428/620; 525/485, 488, 523, 533

(56) References Cited

U.S. PATENT DOCUMENTS

| 5,128,746 A | 7/1992 | Pennisi et al. ............... 357/72 |
| 5,985,043 A | 11/1999 | Zhou et al. ................... 148/24 |
| 5,985,456 A | 11/1999 | Zhou et al. ................. 428/414 |
| 5,985,486 A | 11/1999 | Giron .......................... 429/188 |
| 6,458,472 B1 * | 10/2002 | Konarski et al. .......... 428/620 |

FOREIGN PATENT DOCUMENTS

WO   WO 98/37134   8/1998

* cited by examiner

*Primary Examiner*—Robert E. Sellers, II
(74) *Attorney, Agent, or Firm*—Steven C. Bauman

(57) ABSTRACT

A latent fluxing agent comprising a material which liberates phenol or a carboxylic acid containing compound when heated above 140° C. The latent fluxing agent may be incorporated into a thermoset resin, which includes an epoxy resin. The uncured epoxy resin, which includes the epoxy resin, the latent fluxing agent and an epoxy curing agent are useful as an underfill composition in a method for applying a chip die, having one or more solder balls, to a substrate. The method is used to produce an integrated circuit chip that includes a chip die having electrical contacts arranged in a predetermined pattern and capable of providing electrical engagement with a carrier substrate.

7 Claims, 9 Drawing Sheets

$^1$H NMR spectra (300 MHz; CDCl$_3$) of Diacid 1550 α-alkoxy ester adduct and starting cyclohexyl vinyl ether (CHVE).

Thermogravimetric analysis (TGA) of Diacid 1550/cyclohexyl vinyl ether adduct.
Heating rate = 10°C/minute Thermogravimetric analysis (TGA) of Diacid 1550/2-ethylhexyl vinyl ether adduct.
Heating rate = 10°C/minute Thermogravimetric analysis (TGA) of Diacid 1550/(4-vinyloxy)butyl benzoate adduct. Heating rate = 10°C/minute Thermogravimetric analysis (TGA) of Diacid 1550/4-(1-propenyloxymethyl)-1,3-dioxolan-2-one adduct. Heating rate = 10°C/minute

METHOD OF BONDING DIE CHIP WITH UNDERFILL FLUXING COMPOSITION

CROSS REFERENCE TO RELATED APPLICATIONS

This application claims priority to U.S. Provisional Application No. 60/328,055 filed Oct. 9, 2001, and is a continuation of PCT/US01/31020 filed Oct. 4, 2001 which claims priority to U.S. Provisional Application No. 60/237,541 filed Oct. 4, 2000.

BACKGROUND OF THE INVENTION

1. Field of the Invention

This invention relates to fluxing underfill compositions useful for fluxing metal surfaces in preparation for providing an electrical connection and sealing the space between semiconductor devices (such as chip size or chip scale packages ("CSPs"), ball grid arrays ("BGAs"), land grid arrays ("LGAs"), flip chip assemblies ("FCs") and the like, each of which having a semiconductor chip, such as large scale integration ("LSI")), or semiconductor chips themselves, and a circuit board to which the devices or chips, respectively, are electrically interconnected. More particularly, the present invention relates to underfill compositions capable of releasing a fluxing agent.

2. Brief Description of Related Technology

In recent years, the popularity of small-sized electronic appliances, such as camera-integrated video tape recorders and portable telephone sets, has made size reduction of large scale integration desirable. As a result, chip size or chip scale packages are being used to reduce the size of packages substantially to that of bare chips. Such chip scale packages include a semiconductor chip mounted on a carrier substrate, which improve the characteristics of the electronic device while retaining many of their operating features, thus serving to protect semiconductor bare chips and facilitate testing thereof.

Upside down integrated circuits, commonly referred to as "flip chips", are now gaining popularity as well. Flip chips are manufactured using solder bump technology, in which solder bumps are deposited on solder-wettable metal terminations on a die or chip and a matching pattern of solder-wettable terminations on the substrate. With flip chips, the solder bumps are placed on the integrated circuit terminals while the chip is in wafer form, and then, after singulation, a chip is flipped and aligned to the circuit board substrate. A fluxing agent is applied and the solder bumps are re-flowed by heating to establish bonding between the chip and the substrate, with all the joints being made simultaneously by melting the solder. Typically, eutectic tin/lead solder (melting point 183° C.) or lead/indium solder (melting point 220° C.) are used.

After the solder reflow cycle, residue from the flux would typically be removed in order to prevent semiconductor device corrosion using organic- or aqueous-based solvents, depending on the nature of the flux. The narrow space between the semiconductor device and the substrate, however, renders flux residue removal difficult and time consuming, requiring sophisticated and expensive cleaning systems.

Moreover, when the resulting circuit board assembly is exposed to thermal cycling, the reliability of the solder connection between the circuit board and the chip often becomes suspect. Commonly, after a chip is mounted on a circuit board, the space between the chip and the circuit board is filled with a sealing resin (often referred to as underfill sealing) in order to reinforce against stresses caused by thermal cycling. Such underfill encapsulation has gained considerable acceptance in the electronics industry, with epoxy-based resin materials being most commonly used in such applications. Moreover, the expansion coefficients of the underfill sealing can be adjusted, for example, by the addition of low thermal-expansion fillers such as glass or ceramics, thus reducing the level of thermal stress that develops between the substrate and the underfill sealing. The underfill sealing thus provides structural reinforcement, which delocalizes the thermal expansion stress, thereby improving heat shock properties and enhancing the reliability of the structure.

Also, the underfill material helps adhere the chip to the substrate. As such, the underfill material should exhibit high cohesive strength to the die and the circuit board surface, and retain significant strength within the environment encountered by the electronic device, for example, during heat-up and cool-down cycles associated with on/off powering of the electronics, as well as climatic changes in temperature and humidity.

In an attempt to overcome fluxing residue issues and to eliminate processing steps, underfill sealants incorporating fluxing agents for bonding of the solder bumps have been proposed. For example, U.S. Pat. Nos. 5,985,043 and 5,985,486 disclose polymerizable fluxing agents which act as an adhesive to bond the chip to the substrate. Such polymerizable fluxing agents are based on polycarboxylic acids having olefinic linkages, compositions of which are curable upon exposure to heat. The thinking here is that the underfill sealant incorporating such polymerizable fluxing agent can be applied to the chip during the wafer stage of chip manufacture, often referred to as wafer-applied fluxing underfill, in which a plurality of chips are manufactured in one piece and later cut into individual chips. By pre-applying onto the wafer the fluxing agent/underfill sealant combination, the chip should only need to be placed on the substrate, with solder re-flow and underfill curing occurring to affix the chip thereto.

International Patent Publication No. WO 98/37134 refers to a no-flow underfill encapsulant for flip-chip technology. This encapsulant is based on epoxy resin(s), an anhydride hardener, an accelerator, a surfactant and a fluxing agent, and uses a viscosity-controlling agent, such as fumed silica, and a coupling agent. This encapsulant is reported to provide optimized flow and a curing reaction only after attaining the maximum solder bump reflow temperature of about 190–230° C.

U.S. Pat. No. 5,128,746 (Pennisi) describes a thermally curable adhesive having an acidic fluxing agent for use in reflow soldering an electrical component and a substrate. This adhesive reportedly removes oxide coatings on the metalization of the electrical component, and the adhesive at least partially cures when heated to solder reflow temperatures. The adhesive includes a thermoset resin, a fluxing agent, and a curing agent that reacts with and cures the thermoset resin when the thermally curable adhesive is heated. The exposure of the electrical component and substrate to a low pH environment caused by the acidic fluxing agent, however, can lead to corrosion of metal components.

U.S. Pat. Nos. 5,985,043 and 5,985,456 (Zhou et al.) disclose a thermally curable adhesive composition that includes a fluxing agent that also acts as an adhesive. The composition includes an unsaturated carboxylic acid fluxing agent and may further include a crosslinkable diluent, a source of free radical initiators, and a resin to react with remnant carboxylic acid moieties. However, the presence of the carboxylic acid functionality can result in the metalization of the electrical component being exposed to a low pH environment for extended periods, which can result in undesirable corrosion.

Accordingly, it would be desirable to provide a fluxing underfill composition that fluxes solderable surfaces, such as metal contacts, which the solder will electrically interconnect, and that possesses appropriate cure profiles for curing during the solder reflow cycle. It would be particularly desirable for the fluxing agent to not create an excessive acidic environment for prolonged periods of time, thereby preventing corrosion.

SUMMARY OF THE INVENTION

The present invention is directed to a latent fluxing agent comprising a material which liberates a composition capable of fluxing a solderable surface, when heated above 140° C. The liberated composition includes acidic compounds, such as phenol(s) and derivatives thereof, or a carboxylic acid-containing compound. In particular, the invention is directed to a composition that includes a compound having one or more of the following structures I through VI:

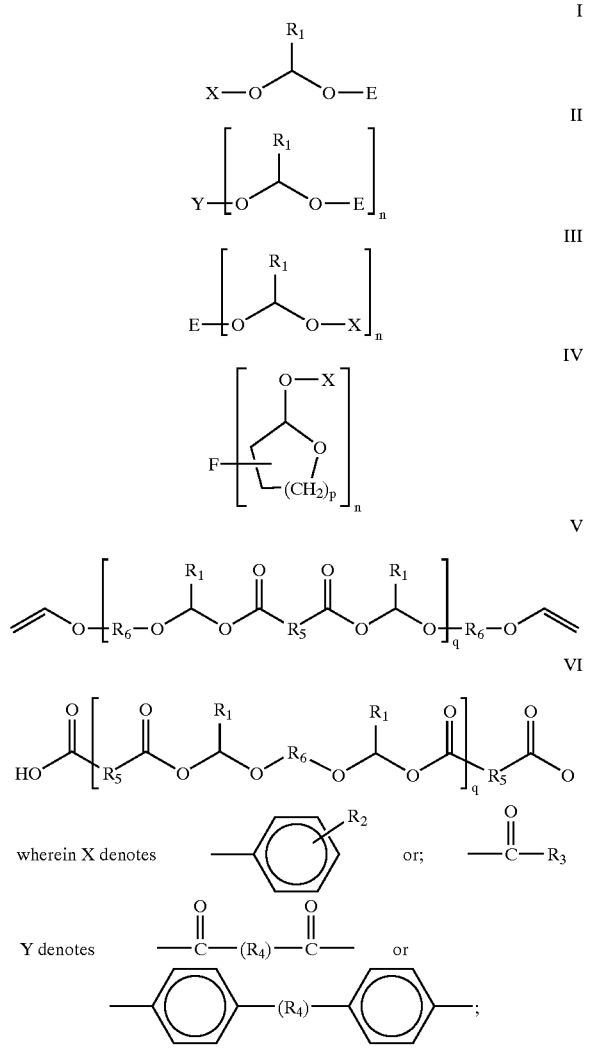

E denotes an organic group derived from a 1-alkenyl ether and may be a hydrocarbon, ether, thioether, ester, thioester, carbamate, amide, or a combination of these groups;

F denotes an organic group fragment derived from a multifunctional 1-cycloalkenyl ether in which the cyclic ether groups are linked though F, and may be a hydrocarbon, ether, thioether, ester, thioester carbamate, amide, or a combination of these groups;

$R_1$ represents a $C_1$–$C_6$ alkyl group;

$R_2$ and $R_3$ are independently selected from hydrogen, substituted or unsubstituted linear or branched $C_{1-22}$ alkyl, alkenyl, aryl, alkaryl, cycloalkyl, alkoxy and phenyl;

$R_4$ is substituted or unsubstituted linear or branched $C_{1-22}$ alkylene, alkenylene, arylene, alkylenearyl, cycloalkylene, alkyleneoxy and phenylene;

$R_5$ and $R_6$ are independently selected from linear or branched $C_{1-22}$ alkyl, alkenyl, aryl, alkaryl, cycloalkyl, alkoxy and phenyl;

n is an integer from 2–30; p represents the integer 1 or 2 and q is an integer from 5–30.

Such a material is desirably an α-alkoxyalkyl ester of a carboxyl-containing compound or an α-alkoxyalkyl phenyl ether.

In particularly desirable embodiments, the group $R_1$ in the above structure includes a reactive group selected from the group consisting of oxirane and hydroxyl, for example, a glycidyl group. Desirably, the composition is a reaction product of a carboxylic acid and a vinyloxy glycidyl ether.

The latent fluxing agent is particularly useful in one-component curable underfill compositions used in the semiconductor industry. As such, the invention is further directed to a curable composition which includes an epoxy resin, a curing agent for the epoxy resin, and a material which liberates a phenolic containing compound or a carboxylic acid containing compound when heated above 140° C. as the latent fluxing agent. Thermoset resins which are a reaction product of the such a composition are further provided.

In particularly desirable embodiments, the latent fluxing agent component includes one or more functional groups capable of incorporating the material into a cured epoxy composition. For example, the material may include a reactive group selected from the group consisting of oxirane and hydroxyl, for incorporation into the epoxy thermoset resin during cure thereof.

In a further embodiment of the present invention, a method for bonding a chip die, which has one or more solder balls, to a substrate is provided. In the method, the chip die is placed in contact with the substrate. A degassed underfill composition is provided between the chip die and the substrate. The underfill composition includes an epoxy resin, a material which liberates a phenolic containing compound or a carboxylic acid containing compound when heated above 140° C., and an epoxy curing agent. The substrate with the chip die and underfill composition is exposed to a temperature greater than 140° C., thereby causing the latent fluxing agent to be released from the composition. Subsequently, reflow of the solder and curing of the underfill composition are accomplished by further heating of the assembly. Desirably, the underfill composition is provided on the chip die prior to placing the chip die in contact with the substrate. The temperature may be applied using a solder reflow oven. An integrated circuit chip prepared according to such a method is further provided.

In a further embodiment, the present invention is directed to an integrated circuit chip including a chip die having electrical contacts arranged in a predetermined pattern and capable of providing electrical engagement with a carrier substrate, with the circuit chip including an underfill composition surrounding the electrical contacts. The underfill composition includes an epoxy resin, a material which liberates phenol or a carboxylic acid containing compound when heated above 140° C.; and an epoxy curing agent, as set forth above. When heated above 140° C., the underfill composition liberates a fluxing agent. Moreover, the electrical contacts are flowable to provide electrical engagement with the carrier substrate, and curing of the underfill composition to adhere the circuit chip to the carrier substrate.

DETAILED DESCRIPTION OF THE INVENTION

Figure 1:
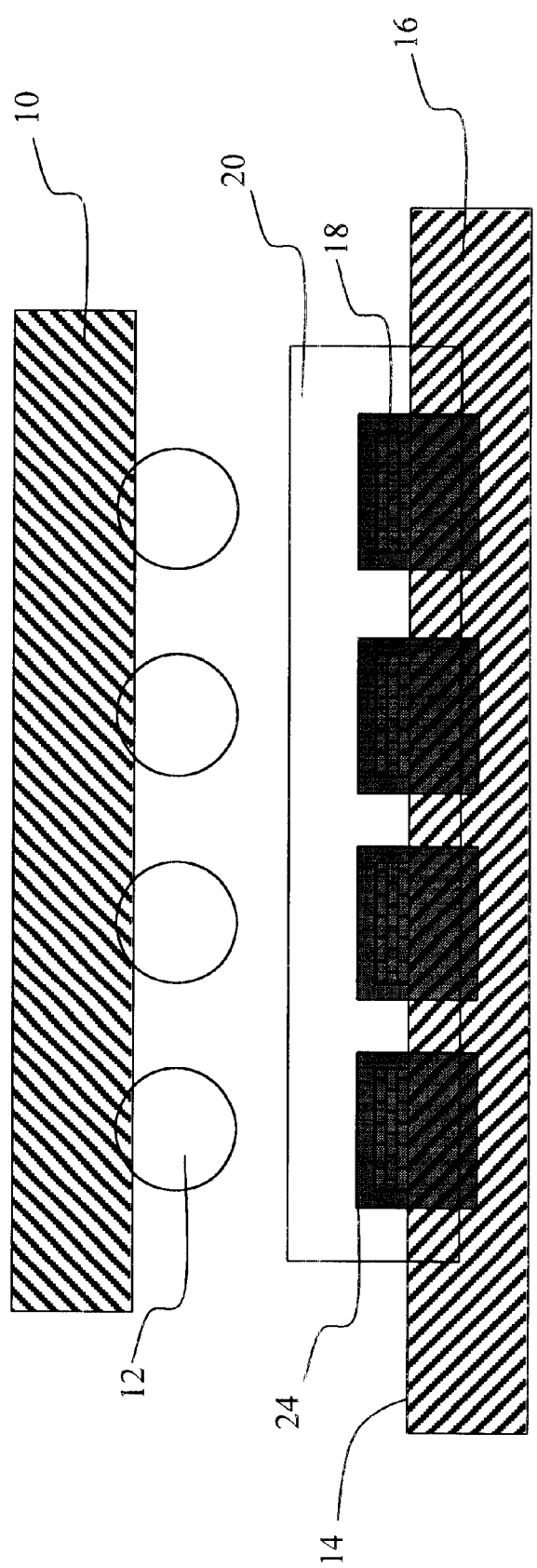
FIG. 1 depicts a cross-sectional view showing a device and substrate prior to attachment of the two surfaces to be interconnected.

Unless otherwise indicated, all numbers or expressions referring to quantities of components, reaction conditions, and the like, used herein are to be understood as modified in all instances by the term "about."

Various numerical ranges are disclosed herein. Because these ranges are continuous, they include every value between the minimum and maximum values. Unless expressly indicated otherwise, the various numerical ranges specified are approximations.

As noted above, the present invention provides a composition which includes a latent fluxing agent, in that the composition includes a material which liberates a phenolic compound or a carboxylic acid containing compound when heated above 140° C. Fluxing agents are commonly used in bonding of electrical circuitry for cleaning the metal surfaces of the electrical contacts by removing dirt and oxide layers to promote proper wetting and adhering of the solder. Phenolic compounds and acidic compounds, such as carboxylic acids, are commonly employed in this manner as fluxing agents. Such phenolic and acidic compounds, however, must be applied to the electrical contacts just prior to soldering of the electrical contacts in order to provide effective fluxing activity. Moreover, when phenolic and/or carboxylic acid fluxing agents are incorporated into underfill compositions used for sealing between a chip and a substrate in an integrated circuit, they can react with the epoxy resin as well as with other curing agents or additives in the composition, thus reducing shelf life or potlife of the formulation. Accordingly, in the present invention, a compound is provided in which the fluxing agent is effectively masked from reaction or interaction with other components in the composition. More particularly, the fluxing agent is in a latent form, with the fluxing agent capable of being released from the compound only upon heating, for example to a temperature above about 140° C., at which time the fluxing agent is liberated from the compound. As such, the latent fluxing agent is a non-acidic composition which liberates a compound including an acidic group or a phenolic group as a fluxing agent when heated above a temperature of about 140° C.

As will be discussed in more detail herein, the present invention is directed to the latent fluxing agent composition itself, and to curable compositions incorporating the latent fluxing agent into an epoxy resin composition. Such compositions are particularly useful as underfill compositions. Accordingly, integrated circuit chips bonded with such compositions and methods for achieving such bonding are also encompassed by the present invention.

The latent fluxing agent of the present invention includes any suitable material that will liberate the fluxing agent, in the form of a phenolic and/or a carboxylic acid, when heated above a predetermined temperature, such as above about 140° C. In particular, the material includes a composition which is a reaction product of a vinyl ether constituent and a phenolic or carboxylic acid constituent, with the reaction product including at least one thermally labile alpha-alkoxyalkyl ester linkage or alpha-alkoxyalkyl phenyl ether linkage. In its most basic structure, the material includes a composition which is a reaction product of a monofunctional vinyl ether and a monofunctional phenolic or carboxylic acid. Such a composition may be represented by the following structure I:

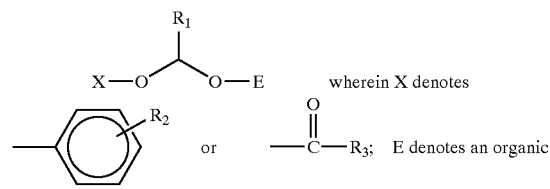

group derived from a 1-alkenyl ether; $R_1$ represents a $C_1$–$C_6$ alkyl group; and $R_2$ and $R_3$ are independently selected from hydrogen, substituted or unsubstituted linear or branched $C_{1-22}$ alkyl, alkenyl, aryl, alkaryl, cycloalkyl, alkoxy and phenyl. In particular, E may be a hydrocarbon, ether, thioether, ester, thioester, carbamate, amide, or a combination of these groups.

Such compositions can be broadly described as α-alkoxyalkyl esters of a carboxyl-containing compound or α-alkoxyalkyl phenyl ethers. The α-alkoxyalkyl ester linkage or the α-alkoxyalkyl phenyl ether linkage, respectively, is a thermally labile linkage, in that when heated to a specific temperature, the linkage will cleave. Such a cleavable linkage establishes a mechanism for masking the phenolic or carboxylic acid until a desired time. Upon heating, the linkage cleaves to release the phenolic or carboxylic acid, which can be used as a fluxing agent as will be described in more detail herein.

The compositions of the present invention are desirably formed by the reaction of a vinyl ether compound with a carboxylic acid or a phenolic compound, producing a composition including an acetal linkage. For example, with respect to a carboxylic acid, such a reaction involves a scheme as follows:

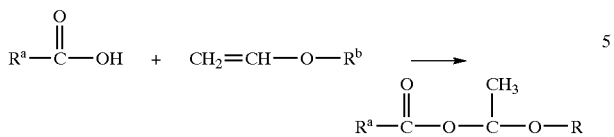

Reactive hydroxy groups in the carboxylic acid compound (or the phenolic compound) react with the vinyl linkage of the vinyl ether, thereby forming an acetal linkage.

Further, monofunctional or multifunctional constituents can be used as the reactants to produce the latent fluxing agent compositions of the present invention. For example, a multifunctional carboxylic acid can be reacted with a vinyl ether compound, according to a scheme as follows:

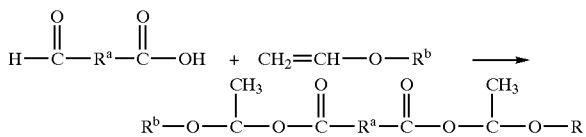

Such a composition may be represented by the following structure II:

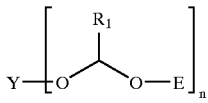

wherein Y denotes 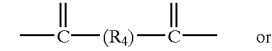 or

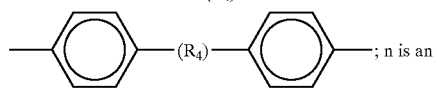; n is an integer from 2–30, desirably from 2–6; $R_4$ is hydrogen, substituted or unsubstituted linear or branched $C_{1-22}$ alkylene, alkenylene, arylene, alkylenearyl, cycloalkylene, alkyleneoxy and phenylene; and E and $R_1$ are as previously described.

Also, multifunctional vinyl ether compounds can be reacted with either a monofunctional or a multifunctional carboxylic acid or phenolic compound. Examples of compositions prepared through the reaction of a multifunctional vinyl ether and a monofunctional phenolic or carboxylic acid may be represented by the following structure III:

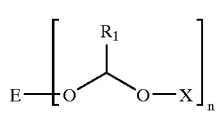

wherein E, X, $R_1$ and n are as previously described. Moreover, the multifunctional vinyl ether constituent may be a cyclic vinyl ether, to produce a composition which may be represented by the following structure IV:

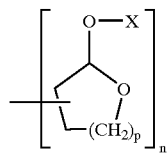

wherein F denotes an organic group fragment derived from a multifunctional 1-cycloalkenyl ether in which the cyclic ether groups are linked though F, p represents the integer 1 or 2, and X and n are as previously described. F may be attached to the ring portion of the structure at any carbon position other than the carbon atom located between the two oxygen atoms of the acetal fragment or the carbon atom alpha to this position. More specifically, F may be a hydrocarbon, ether, thioether, ester, thioester carbamate, amide, or a combination of these groups; it may also be a low molar mass entity or an oligomeric or a polymeric species.

More particularly, a multifunctional carboxylic acid and a multifunctional vinyl ether compound can be provided for reaction, with a polymerization reaction occurring to form a vinyl ether terminated polymer. In such reactions, it is desirable to maintain a stoichiometric amount of the vinyl ether constituent in order to prevent the formation of the corresponding carboxylic acid functionalized polymer. Moreover, the degree of polymerization is desirably maintained relatively low, such as a number average degree of polymerization of about 5 to 10. Such a composition may be represented by the following structure V:

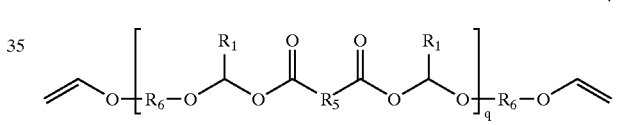

wherein $R_5$ and $R_6$ are independently selected from linear or branched $C_{1-22}$ alkylene, alkenylene, arylene, alkylenearyl, cycloalkylene, alkyleneoxy and phenylene; q is an integer from 5–30, and $R_1$ is as previously described.

In addition, a polymeric structure with terminal carboxylic acid groups may also be provided as the reaction product of a multifunctional carboxylic acid and a multifunctional vinyl ether compound. Such a carboxylic acid terminated polymer may be obtained when the reaction is carried out with a stoichiometric excess of carboxylic acid. The general structure of such a carboxylic acid terminated polymer may be represented by the following structure VI:

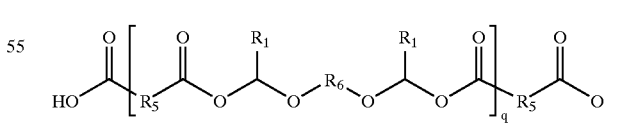

wherein $R_5$ and $R_6$ are independently selected from linear or branched $C_{1-22}$ alkylene, alkenylene, arylene, alkylenearyl, cycloalkylene, alkyleneoxy and phenylene; q is an integer from 5–30, and $R_1$ is as previously described.

The latent fluxing agent of the present invention is particularly useful in a curable composition for use as an underfill composition for a circuit chip. Such a curable composition may be a one component curable composition including an epoxy resin, a curing agent for the epoxy resin, and the latent fluxing agent including a material which liberates phenol or a carboxylic acid-containing compound when heated above 140° C. In such an embodiment, the latent fluxing agent includes one or more compounds as described above, such as in structures I through VI above.

As noted, the composition liberates a phenolic and/or a carboxylic acid containing compound when the resin is heated above 140° C., for use as a fluxing agent. While the exact mechanism of the decomposition reaction is not entirely understood, it is believed that such compounds, when exposed to temperatures above 140° C., results in the α-alkoxyalkyl ester or the α-alkoxyalkyl phenyl ether breaking down into its substituents. For example, the α-alkoxyalkyl ester may break down upon heating such that a carboxylic acid component and a vinyl ether component are released. The carboxylic acid component functions as a fluxing agent, cleaning the metal contacts of the semiconductor assembly, as will be discussed in more detail herein.

The vinyl ether component when released may undesirably interact with the epoxy component during curing of the epoxy component. In particular, it is believed that vinyl ethers may cause undesirable effects in epoxy compositions, such as gas evolution, resulting in voids in the cured epoxy thermoset structure. In order to overcome such effects, it is desirable for the vinyl ether substituent to include a suitable reactive group, for incorporating into the epoxy resin upon curing thereof such that, upon breaking down, the vinyl ether substituent of the composition maintains the reactive group. Desirably, such a reactive group is included by providing $R^1$ in structures I through VI above with a reactive group, such as oxirane, thiirane, hydroxyl, amino or mercapto, and in particular, with a glycidyl group. This can be accomplished, for example, by providing the latent fluxing agent as a reaction product of a carboxylic acid and a vinyl glycidyl ether. Such a reaction is desirably controlled to prevent reaction of the epoxy group and to produce an acetal linkage through reaction of the carboxylic acid and the vinyl group, which results in the latent fluxing agent of the present invention including an α-alkoxyalkyl ester having an epoxy group on one end thereof. As such, the decomposition products of the latent fluxing agent result in an epoxy vinyl ether compound having an epoxy functionality. The epoxy group is capable of binding into the epoxy network during subsequent curing of the epoxy component of the composition, and is therefore readily incorporated into the cured thermoset resin.

As noted, the latent fluxing agent may be provided as the reaction product of a carboxylic acid and a vinyl ether. Mono-alkenyl carboxylic acids useful in the production of compounds useful in the present invention are organic compounds containing one alkenyl group and one carboxylic acid group in the same molecule. Such compounds be represented by, but are not limited to, the following structures:

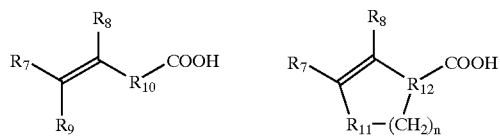

wherein $R_7$, $R_8$ and $R_9$ are independently selected from H, $C_1$–$C_{20}$ alkyl, alkenyl, cycloalkyl, aryl, alkaryl, and alkoxy; $R_{10}$, which may or may not be present, is $C_1$–$C_{20}$ alkylene, alkenylene, cycloalkylene, arylene, alkylenearyl, and alkyleneoxy; $R_{11}$ and $R_{12}$ represent $C_1$–$C_6$ alkylene that may be further linked to produce bicyclic structures. "n" is an integer having a value between 1 and 8.

The mono-alkenyl carboxylic acid may be selected from the following: 3-cyclohexene-1-carboxylic acid, 2-hexeneoic acid, 3-hexeneoic acid, 4-hexeneoic acid, acrylic acid, methacrylic acid, crotonic acid, vinyl acetic acid, tiglic acid, 3,3-dimethylacrylic acid, trans-2-pentenoic acid, 4-pentenoic acid, trans-2-methyl-2-pentenoic acid, 2,2-dimethyl-4-pentenoic acid, trans-2-hexenoic acid, trans-3-hexenoic acid, 2-ethyl-2-hexenoic acid, 6-heptenoic acid, 2-octenoic acid, (+/−)-citronellic acid, (R)-(+)-citronellic acid, (S)-(−)-citronellic acid, undecylenic acid, myristolic acid, palmitoleic acid, oleic acid, elaidic acid, cis-11-eicosenoic acid, erucic acid, nervonic acid, cis-3-chloroacrylic acid, trans-3-chloroacrylic acid, 2-bromoacrylic acid, 2-(trifluoromethyl)acrylic acid, 2-(bromomethyl)acrylic acid, 2-cyclopentene-1-acetic acid, (1R-trans)-2-(bromomethyl)-2-methyl-3-methylenecyclopentaneacetic acid, 2-acetamidoacrylic acid, 5-norbornene-2-carboxylic acid, 3-(phenylthio)acrylic acid, trans-styrylacetic acid, trans-cinnamic acid, alpha-methylcinnamic acid, alpha-phenylcinnamic acid, 2-(trifluoromethyl)cinnamic acid, 2-chlorocinnamic acid, 2-methoxycinnamic acid, cis-2-methoxycinnamic acid, 3-methoxycinnamic acid, 4-methylcinnamic acid, 4-methoxycinnamic acid, 2,5-dimethoxycinnamic acid, 3,4-(methylenedioxy)cinnamic acid, 2,4,5-trimethoxycinnamic acid, 3-methylindene-2-carboxylic acid, and trans-3-(4-methylbenzoyl)acrylic acid.

Non-limiting examples of non-aromatic carboxylic acids useful for preparation of the latent fluxing agents of the present invention include oxalic acid, malonic acid, methylmalonic acid, ethylmalonic acid, butylmalonic acid, dimethylmalonic acid, diethylmalonic acid, succinic acid, methylsuccinic acid, 2,2-dimethylsuccinic acid, 2-ethyl-2-methylsuccinic acid, 2,3-dimethylsuccinic acid, meso-2,3-dimethylsuccinic acid, glutaric acid, (+/−)-2-methylglutaric acid, 3-methylglutaric acid, 2,2-dimethylglutaric acid, 2,4-dimethylglutaric acid, 3,3-dimethylglutaric acid, adipic acid, 3-methyladipic acid, (R)-(+)-3-methyladipic acid, 2,2,5,5-tetramethylhexanedioic acid, pimelic acid, suberic acid, azelaic acid, 1,10-decanedicarboxylic acid, sebacic acid, 1,11-undecanedicarboxylic acid, undecanedioic acid, 1,12-dodecanedicarboxylic acid, hexadecanedioic acid, docosanedioic acid, tetracosanedioic acid, tricarballylic acid, beta-methyltricarballylic acid, 1,2,3,4-butanetetracarboxylic acid, itaconic acid, maleic acid, fumaric acid, citraconic acid, mesaconic acid, trans-glutatonic acid, trans-beta-hydromuconic acid, trans-traumatic acid, trans,trans-muconic acid, cis-aconitic acid, trans aconitic acid, (+/−)-chlorosuccinic acid, (+/−)-bromosuccinic acid, meso-2,3-dibromosuccinic acid, hexa fluoroglutaric acid, perfluoroadipic acid hydrate, dibromomaleic acid, DL-malic acid, D-malic acid, L-malic acid, (R)-(−)-citramalic acid, (S)-(+)-citramalic acid, (+/−)-2-isopropylmalic acid, 3-hydroxy-3-methylglutaric acid, ketomalonic acid monohydrate, DL-tartaric acid, L-tartaric acid, D-tartaric acid, mucic acid, citric acid, citric acid monohydrate, dihydroflumaric acid hydrate, tetrahydrofuran-2,3,4,5-tetracarboxylic acid, mercaptosuccinic acid, meso-2,3-dimercaptosuccinic acid, thiodiglycolic acid, 3,3'-thiodipropionic acid, 3,3'-dithiodipropionic acid, 3-carboxypropyl disulfide, (+/−)-2-(carboxymethylthio) succinic acid, 2,2',2'',2'''-[1,2-ethanediylidenetetrakis(thio)]-tetrakisacetic acid, nitromethanetrispropionic acid, oxalacetic acid, 2-ketoglutaric acid, 2-oxoadipic acid hydrate, 1,3-acetonedicarboxylic acid, 3-oxoadipic acid, 4-ketopimelic acid, 5-oxoazelaic acid, chelidonic acid, 1,1-cyclopropanedicarboxylic acid, 1,1-cyclobutanedicarboxylic acid, (+/−)-trans-1,2-cyclobutanedicarboxylic acid, trans-DL-1,2-cyclopentanedicarboxylic acid, 3,3-tetramethyleneglutaric acid, (1R.3S)-(+)-camphoric acid, (1S.3R)-(−)-camphoric acid, (+/−)-cyclohexylsuccinic acid, 1,1-cyclohexanediacetic acid, (+/−)-trans-1,2-cyclohexanedicarboxylic acid, (+/−)-1,3-cyclohexanedicarboxylic acid, trans-1,2-cyclohexanedicarboxylic acid, 1,4-cyclohexanedicarboxylic acid, 1,3-adamantanedicarboxylic acid, 3-methylenecyclopropane-trans-1,2-dicarboxylic acid, cis-5-norbomene-endo-2,3-dicarboxylic acid, 1,3,5-cyclohexanetricarboxylic acid, 1,3,5-cyclohexanetricarboxylic acid, kemp's triacid, (1alpha.3alpha.5beta)-1,3,5-trimethyl-1,3,5-cyclohexanetricarboxylic acid, 1,2,3,4-cyclobutanetetracarboxylic acid, and 1,2,3,4,5,6-cyclohexanehexacarboxylic acid monohydrate.

Non-limiting examples of aromatic carboxylic acids useful for preparation of the latent fluxing agents of the present invention include phenylmalonic acid, benzylmalonic acid, phenylsuccinic acid, 3-phenylglutaric acid, 1,2-phenylenediacetic acid, homophthalic acid, 1,3-phenylenediacetic acid, 4-carboxyphenoxyacetic acid, 1,4-phenylenediacetic acid, 2,5-dihydroxy-1,4-benzenediacetic acid, 1,4-phenylenediacrylic acid, phthalic acid, isophthalic acid, 1,2,3-benzenetricarboxylic acid hydrate, terephthalic acid, 1,2,4-benzenetricarboxylic acid, 1,2,4,5-benzenetetracarboxylic acid, mellitic acid, 3-(carboxymethylaminomethyl)-4-hydroxybenzoic acid, 4-methylphthalic acid, 2-bromoterephthalic acid, 4-bromoisophthalic acid, 4-hydroxyisophthalic acid, 4-nitrophthalic acid, nitrophthalic acid, 1,4-phenylenedipropionic acid, 5-tert-butylisophthalic acid, 5-hydroxyisophthalic acid, 5-nitroisophthalic acid, 5-(4-carboxy-2-nitrophenoxy)-isophthalic acid, diphenic acid, 4,4'-biphenyldicarboxylic acid, 5,5'dithiobis(2-nitrobenzoic acid), 4-[4-(2-carboxybenozoyl)phenyl]-butyric acid, pamoic acid, 1,4-naphthalenedicarboxylic acid, 2,3-naphthalenedicarboxylic acid, 2,6-naphthalenedicarboxylic acid, 1,4,5,8-naphthalene-tetracarboxylic acid hydrate, and 2,7-di-tert-butyl-9,9-dimethyl-4,5-xanthenedicarboxylic acid.

A particularly useful carboxylic acid for the preparation of the latent fluxing agents of the present invention is DIACID 1550®, a monocyclic $C_{21}$ dicarboxylic acid product derived from tall oil fatty acids, commercially available from Westvaco Corporation.

Non-limiting examples of phenolic compounds useful for the preparation of the fluxing agents of the present invention include phenolic novalacs and cresol novalacs.

Vinyl ethers useful in the preparation of the compounds of the present invention include mono-functional 1-alkenyl ethers and multi-functional 1-alkenyl ethers, which may be represented by the following structure:

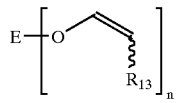

wherein $R_{13}$ is hydrogen or $C_1$–$C_5$ alkyl group and E and n are as already described.

Suitable multifunctional 1-alkenyl ether compounds include the following: 1,6-hexanediol divinylether, 1,4-cyclohexane dimethanol divinyl ether, trimethylolpropane trivinylether, diethyleneglycol divinyl ether, polyoxyethylene divinyl ether, ethyleneglycol divinyl ether, tetraethyleneglycol divinyl ether, bis[4-(vinyloxy)butyl]isophthalate, bis[4-(vinyloxymethyl)cyclohexylmethyl]glutarate, bis[4-(vinyloxy)butyl]succinate, bis[4-(vinyloxy)butyl]adipate, bis[4-(vinyloxy)butyl](methylene di-4,1-phenylene) biscarbamate, tris[4-(vinyloxy)butyl]trimellitate, butanediol divinyl ether, nonandiol divinylether, cyclohexanediol divinylether, pentaerythritol-tetravinyl ether, 1,4-dipropenoxybutane, 1,6-dipropenoxyhexane, 1,6-dipropenoxyoctane, 1,10-dipropenoxydecane, diethyleneglycoldipropenyl ether, neopentylglycoldipropenyl ether, triethyleneglycoldipropenyl ether, trimethylolpropanetripropenyl ether, 1,2,3-tripropenoxypropane, pentaerythritoltetrapropenyl ether, and sorbitolhexapropenyl ether.

Non-limiting examples of additional vinyl ethers useful for preparation of the latent fluxing agents of the present invention include cyclohexyl vinyl ether; 2-ethylhexyl vinyl ether; (4-vinyloxy)butyl benzoate; 4-(1-propenyloxymethyl)-1,3-dioxolan-2-one; and poly-THF-divinyl ether 290.

Also useful are those monomeric vinyl ethers available from Allied Signal Corp. under the tradename VECTOMER, such as 1,3-benzenedicarboxylic acid, bis[4-(ethenyloxy)butyl]ester (VECTOMER VE 4010); pentanedioic acid, bis[[4-[(ethenyloxy)methyl]cyclohexyl]methyl]ester (VECTOMER VE 4020); butanedioic acid, bis[4-(ethenyloxy)butyl]ester (VECTOMER VE 4030); hexanedioic acid, bis[4-(ethenyloxy)butyl]ester (VECTOMER VE 4060); carbamic acid, (methylenedi-4,1-phenylene)bis-bis[4-(ethenyloxy)butyl]ester (VECTOMER VE 4210); carbamic acid, (4-methyl-1,3-phenylene)bis-, bis[4-(ethenyloxy)butyl]ester (VECTOMER VE 4220); and 1,2,4-benzenetricarboxylic acid tris[4-(ethenyloxy)butyl]ester (VECTOMER VE 5015).

Other useful vinyl ethers including oligomeric vinyl ethers available from Allied Signal Corp. under the tradenames VECTOMER VE 1214, VECTOMER VE 1221, VECTOMER VE 1222, VECTOMER VE 1312, VECTOMER VE 2010, VECTOMER VE 2020, VECTOMER VE 2031 and VECTOMER VE 2032.

Cyclic vinyl ethers may also be used in the preparation of the latent fluxing agents of the present invention. Multifunctional 1-cycloalkenyl ethers useful in the preparation of the compounds of the present invention may be represented by the following structure:

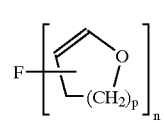

IV wherein F, p and n are as already described.

Non-limiting examples of cyclic vinyl ethers useful in the present invention include 3,4-dihydro-2H-pyran, and 2-(3, 4-dihydropyramyl)methyl-3,4-dihydropyran-2-carboxylate.

An example of a useful vinyl ether including epoxy functionality is 2-vinyloxyethyl glycidyl ether.

As noted, the latent fluxing agent may be incorporated into a curable composition. The curable resin component may be selected from any known resin. Desirably, the curable resin may be any common epoxy resin, such as a multifunctional epoxy resin. Examples of suitable epoxy resins that may be used include, but are not limited to, bisphenol-A-type epoxy resin (such as RE-310-S from Nippon Kayaku, Japan, or EPON 828 or EPON 1002f from Shell Chemical Co.), bisphenol-F-type epoxy resin (such as RE-404-S from Nippon Kayaku, Japan), phenol novolac-type epoxy resin and cresol novolac-type epoxy resin (such as ARALDITE ECN 1871 from Ciba Specialty Chemicals, Hawthorne, N.Y.).

Other suitable epoxy resins include polyepoxy compounds based on aromatic amines and epichlorohydrin, such as N,N,N',N'-tetraglycidyl-4,4'-diaminodiphenyl methane; N-diglycidyl-4-aminophenyl glycidyl ether; and N,N,N',N'-tetraglycidyl-1,3-propylene bis-4-aminobenzoate.

The epoxy resins suitable for use herein also include polyglycidyl derivatives of phenolic compounds, such as those available commercially under the tradename EPON, such as EPON 1031 from Shell Chemical Co.; DER 331, "DER" 332, DER 334 and DER 542 from Dow Chemical Co. and BREN-S from Nippon Kayaku, Japan. Other suitable epoxy resins include polyepoxides prepared from polyols and the like and polyglycidyl derivatives of phenol-formaldehyde novolacs, the latter of which are available commercially under the tradename DEN, such as DEN 431, DEN 438, and DEN 439 from Dow Chemical. Cresol analogs are also available commercially under the tradename ARALDITE, such as ARALDITE ECN 1235, ARALDITE ECN 1273 and ARALDITE ECN 1299 from Ciba Specialty Chemicals. SU-8 is believed to be a cresol novolac epoxy available from Interez, Inc. Polyglycidyl adducts of amines, aminoalcohols and polycarboxylic acids are also useful in this invention, commercially available resins of which include GLYAMINE 135, GLYAMINE 125 and GLYAMINE 115 from F.I.C. Corporation; ARALDITE MY-720, ARALDITE 0500 and ARALDITE 0510 from Ciba Specialty Chemicals and PGA-X and PGA-C from Sherwin-Williams Co. Copolymers of epichlorohydrin and bisphenol A as well, such as EPON 1001 and EPON 1009 from Shell Chemical Co., may be used. Combinations of the different epoxy resins are also desirable for use herein.

The curable composition of the present invention further includes a compound for effecting polymerization and cure of the epoxy resin component, such as an epoxy curing agent or catalyst, or combinations of a curing agent and catalyst. Desirable materials include anhydride-containing compounds; nitrogen-containing compounds such as amine compounds, amide compounds and imidazole compounds; polyfunctional phenols; carboxylic acids and thiols; and combinations thereof. More particularly, the epoxy resin component may be cured using stoichiometric amounts of a curing agent, such as anhydrides, primary and secondary amines, polyfunctional phenols, carboxylic acids, and thiols; may be cured using non-stoichiometric amounts of catalysts, such as tertiary amines and imidazoles; or may be cured through a combination of such curing agents and catalysts.

Anhydride compounds are desirably included as the curing agent for curing of the epoxy resin component. Non-limiting examples of appropriate anhydride compounds for use herein include mono- and poly-anhydrides, such as hexahydrophthalic anhydride ("HHPA") and methyl hexahydrophthalic anhydride ("MHHPA") (commercially available from Lindau Chemicals, Inc., Columbia, S.C., used individually or as a combination, which combination is available under the trade designation LINDRIDE 62C), 5-(2,5-dioxotetrahydrol)-3-methyl-3-cyclohexene-1,2-dicarboxylic dianhydride (commercially available from ChrisKev Co., Leewood, Kans. under the trade designation B-4400), nadic methyl anhydride, 3,3',4,4'-benzophenone tetracarboxylic dianhydride ("BTDA"), pyromellitic dianhydride ("PMDA"), 3,3',4,4'-biphenyl tetracarboxylic dianhydride ("s-BPDA"), 2,2'-bis-(3,4-carboxyphenyl) hexafluoropropane dianhydride ("6FDA"), 4,4'-oxydiphthalic anhydride ("ODPA"), 3,3',4,4'-diphenylsulfone tetracarboxylic dianhydride ("DSDA"), ethylene glycol bis (anhydro-trimellitate) ("TMEG-200", "TMEG-100") and combinations thereof. Combinations of these anhydride compounds are also desirable for use in the compositions of the present invention.

In addition to or instead of the anhydride compound, one or more nitrogen-containing compounds may be provided as an epoxy curing agent or an epoxy cure catalyst. Such compounds are ordinarily one or more amine compounds, including polyamines and di- and tri-aza compounds, amide compounds, imidazole compounds and combinations thereof. More particularly, primary and secondary amine curing agents are coreactive with the epoxide group of the epoxy component. They act as comonomers with the epoxide and are incorporated into the network polymer by a step-growth mechanism. Primary and second amine curing agents are typically used in an amount of about 0.15 to about 1.5 equivalents of amine per equivalent of epoxide. Desirably, primary and secondary amine curing agents are used in an amount of about 1 equivalent of amine per equivalent of epoxide, i.e., two moles of epoxide per mole of primary amine and one mole of epoxide per mole of secondary amine. Primary amines are generally desired over secondary amines, although blends may be employed.

In contrast, tertiary amines, imidazoles, amine-boron trihalide complexes, quaternary ammonium salts, and related curing agents are generally employed as catalysts or initiators of epoxide polymerization. The mechanism is essentially that of an addition homopolymerization reaction and the structure of the cured product is that of a crosslinked polyether. Generally only small amounts of such materials are used (typically 0.01–10% by weight of epoxy) and the amine may be incorporated into the polymer network at the chain ends. Quarternary phosphonium salts may also be useful as curing agents which are generally employed as catalysts or initiators of epoxide polymerization.

The nitrogen-containing compound desirably includes di-aza compounds or tri-aza compounds. Examples of the di- or tri-aza compounds include:

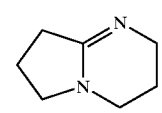

(II)

1,5-diazabicyclo[4.3.0]non-5-ene

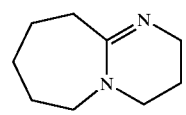

(III)

1,8-diazabicyclo[5.4.0]undec-7-ene ("DBU");

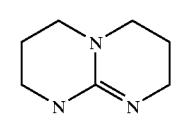

(IV)

1,5,7-triazabicyclo[4.4.0]dec-5-ene;
and the bicyclo mono- and di-aza compounds:

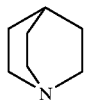

quinuclidine; and

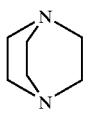

1,4-diazabicyclo[2.2.2.]octane.

Examples of the amine compounds include the following alkyl poly amines: diethylenetriamine, triethylenetetraamine, diethylaminopropylamine, isophoronediamine and menthenediamine; and the aromatic polyamines: m-xylenediamine, diaminodiphenylamine and quinoxaline.

Examples of amide compounds include cyano-functionalized amides, such as dicyandiamide.

The imidazole compounds may be chosen from imidazole, isoimidazole, and substituted imidazoles, such as alkyl-substituted imidazoles (e.g., 2-methyl imidazole, 2-ethyl-4-methylimidazole, 2,4-dimethylimidazole, butylimidazole, 2-undecenylimidazole, 1-vinyl-2-methylimidazole, 2-n-heptadecylimidazole, 2-undecylimidazole, 2-heptadecylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole, and additional products of an imidazole and trimellitic acid, 2-n-heptadecyl-4-methylimidazole and the like, generally where each alkyl substituent contains up to about 17 carbon atoms and desirably up to about 6 carbon atoms, and aryl-substituted imidazoles, e.g., phenylimidazole, benzylimidazole, 2-methyl-4,5-diphenylimidazole, 2,3,5-triphenylimidazole, 2-styrylimidazole, 1-(dodecyl benzyl)-2-methylimidazole, 2-(2-hydroxyl-4-t-butylphenyl)-4,5-diphenylimidazole, 2-(2-methoxyphenyl)-4,5-diphenylimidazole, 2-(3-hydroxyphenyl)-4,5-diphenylimidazole, 2-(p-dimethylaminophenyl)-4,5-diphenylimidazole, 2-(2-hydroxyphenyl)-4,5-diphenylimidazole, di(4,5-diphenyl-2-imidazole)-benzene-1,4,2-naphthyl-4,5-diphenylimidazole, 1-benzyl-2-methylimidazole, 2-p-methoxystyrylimidazole, and the like, generally where each aryl substituent contains up to about 10 carbon atoms and desirably up to about 8 carbon atoms.

Examples of commercial imidazole compounds are available from Air Products, Allentown, Pa. under the trade designation CUREZOL 1B2MZ, from Synthron, Inc., Morganton, N.C. under the trade designation ACTIRON NXJ-60 and from Borregaard Synthesis, Newburyport, Mass., under the trade designation CURIMID CN. Combinations of these amine compounds are also desirable for use in the compositions of the present invention.

The one component curable composition may further include an epoxy resin adduct of a carboxyl terminated toughening agent. Any suitable epoxy resin adduct of a carboxyl terminated toughening agent may be used in the present invention. A specific example of a suitable epoxy resin adduct of a carboxyl terminated toughening agent includes, but is not limited to, an epoxy resin adduct of a carboxyl terminated synthetic rubber. In an embodiment of the present invention, the synthetic rubber is one or more of polybutadiene, styrene-butadiene rubber, butadiene-acrylonitrile rubber and acrylonitrile-butadiene-styrene rubber.

Also, the one component curable composition may include an inorganic filler material. Any suitable inorganic filler material may be used in the present invention. Specific examples of suitable inorganic filler materials include, but are not limited to, materials constructed of or containing reinforcing silicas, aluminum oxide, silicon nitride, aluminum nitride, silica-coated aluminum nitride and boron nitride.

Other additives may be included in the inventive compositions, such as a reactive co-monomer component (e.g., a reactive diluent), air release agents (like those available commercially from BYK-Chemie, Wallingford, Conn. under the BYK trade name, such as BYK-515 or BYK-555), leveling agents, dyes, pigments, adhesion promoters and the like.

Appropriate reactive diluents for use herein may include monofunctional or certain multifunctional epoxy resins. The reactive diluent should have a viscosity which is lower than that of the epoxy resin component. Ordinarily, the reactive diluent should have a viscosity less than about 250 cPs. In the event that such a monofunctional epoxy resin is included as a reactive diluent, such resin should be employed in an amount of up to about 50 weight percent, based on weight of the epoxy resin component. The monofunctional epoxy resin should have an epoxy group with an alkyl group of about 6 to about 28 carbon atoms, examples of which include $C_{6-28}$ alkyl glycidyl ethers, $C_{6-28}$ fatty acid glycidyl esters and $C_{6-28}$ alkylphenol glycidyl ethers.

Commercially available monofunctional epoxy resin reactive diluents include those from Pacific Epoxy Polymers, Richmond, Mich., under the trade designations PEP-6770 (glycidyl ester of neodecandoic acid), PEP-6740 (phenyl glycidyl ether) and PEP-6741 (butyl glycidyl ether).

Commercially available multifunctional epoxy resin reactive diluents include those from Pacific Epoxy Polymers, under the trade designations PEP-6752 (trimethylolpropane triglycidyl ether) and PEP-6760 (diglycidyl aniline).

Air release agents appear to provide beneficial affects on wetting the solder. The air release agent seems to reduce the surface tension on the solder, which is important in solder fluxing. When used, the air release agent may be used in an amount of up to about 1 weight percent, based on the total weight of the composition.

In addition, adhesion promoters, such as the silanes, glycidoxypropyl trimethoxysilane (commercially available from OSI under the trade designation A-187), gamma-amino propyl triethoxysilane (commercially available from OSI under the trade designation A-1100) or a trimethoxysilyl propylated isocyanurate (commercially available from OSI under the trade name SILQUEST, such as Y-11597), may be used.

When used, the adhesion promoters should be included in the inventive compositions in an amount of up to about 2 weight percent.

It is noted that various epoxy compounds have been disclosed as useful for the epoxy component or as various additives for the composition of the present invention, such as toughening agents, reactive diluents, fillers, and the like. While such epoxy compounds may include carboxyl groups or may include phenol glycidyl ethers, they are meant for reaction in the epoxy composition. Such compounds, therefore, do not break down into substituents at about 140° C., and are therefore not capable of releasing a carboxylic acid or a phenol when heated to a temperature above about 140° C. As such, those epoxy-containing compounds disclosed as useful toughening agents, reactive diluents, fillers, and the like, are different than the compounds useful as the latent fluxing agent of the present invention.

The epoxy resin content in the one component curable composition is at least 10 percent by weight, often times at least 20 percent by weight and typically at least 30 percent by weight of the one component curable composition. When the epoxy resin content is too low, the cured thermoset resin may have insufficient strength. The epoxy resin content in the one component curable composition is not more than 99 percent by weight, often times not more than 90 percent by weight and typically not more than 70 percent by weight of the one component curable composition. When the epoxy resin content is too high, the cured thermoset resin may be too brittle. The epoxy resin may be present in the one component curable composition in any range of values inclusive of those stated above. Desirably, the epoxy resin should be included in an amount within the range of about 15 to about 75 weight percent, such as about 40 to about 60 weight percent, based on the total weight of the composition. In the case of bisphenol-F-type epoxy resin, desirably, the amount thereof should be in the range of from about 35 to about 65 weight percent, such as about 40 to about 50 weight percent of the total composition.

The latent fluxing agent content in the one component curable composition is at least 1 percent by weight, often times at least 10 percent by weight and typically at least 30 percent by weight of the one component curable composition. When the latent fluxing agent is present at too low a level, it may not provide adequate fluxing of the metalization of an electrical component. The latent fluxing agent content in the one component curable composition is not more than 90 percent by weight, often times not more than 80 percent by weight and typically not more than 70 percent by weight of the one component curable composition. When the latent fluxing agent content is too high, the cured thermoset resin may be too soft. The latent fluxing agent may be present in the one component curable composition in any range of values inclusive of those stated above. Desirably, the latent fluxing agent is included in an amount of about 4 to about 20 weight percent, such as about 10 to about 15 weight percent, based on the total weight of the composition.

As noted above, the compound which effects cure of the epoxy monomer is provided in an amount to effect complete curing of the epoxy monomer. When such a compound is an epoxy curing agent, it is present in a stoichiometric amount with respect to epoxy monomer, with the curing agent being desirably included in an amount of from about 0.1 to about 5 equivalents per equivalent of epoxide, desirably about 0.15 to about 1.5 equivalents per equivalent of epoxide. For example, when the epoxy curing agent is an anhydride curing agent, it is desirably included in an amount within the range of about 0.5 to about 1.3 equivalents of anhydride per equivalent of epoxide. When the epoxy curing agent is a primary or secondary amine, it is desirably included in an amount within the range of about 0.5 to about 2.0 equivalents of amine per equivalent of epoxide. It is noted that such equivalent amounts are based on epoxy equivalent of the total epoxide content, whether such epoxide is present in the epoxy resin or in the latent fluxing agent which may include an epoxy component within the structure thereof, as discussed. Moreover, when a cure catalyst is employed, whether in addition to or instead of the epoxy curing agent, such a catalyst is desirably included in an amount of from about 0.02 to about 20 percent by weight o the epoxy component.

When the inorganic filler material, epoxy resin adduct of a carboxyl terminated toughening agent and/or other additives are included in the one component curable composition, they are independently included in an amount of at least 0.1 percent by weight, often times at least 0.5 percent by weight and typically at least 1 percent by weight and not more than 70 percent by weight, often times not more than 35 percent by weight and typically not more than 20 percent by weight. The inorganic filler material and/or epoxy resin adduct of a carboxyl terminated toughening agent may independently be present in the one component curable composition in any range of values inclusive of those stated above.

The sum of the weight percentages of the epoxy resin, latent fluxing agent, and the epoxy curing agent, as well as any additional additives as noted above, will always total 100 percent by weight of the one component curable composition.

The underfill compositions including the latent fluxing agent are particularly useful in assembling microelectronics. Accordingly, the present invention also provides a method for applying a chip die, which has one or more solder bumps, to a substrate.

The chip die may be constructed of any material known in the art. For example, the chip die may be constructed of silicon, germanium or the like. The chip die may also be coated with a material which is capable of passivating environmental corrosion, such as a polyimide-, polybenzocyclobutane- or silicone nitride-based material. Desirably, the chip die is constructed as a flip-chip type of circuite chip.

The substrate may also be constructed of any material known in the art. For example, the substrate may be constructed from ceramic substrates including $Al_2O_3$, $Si_3N_4$, and mullite ($Al_2O_3$—$SiO_2$); substrates or tapes of heat-resistant resins, such as polyimides; substrates of glass-reinforced epoxy; substrates of acrylonitrile-butadiene-styrene (ABS); and phenolic substrates, and the like.

The chip die includes circuitry on a surface thereof, including a plurality of electrical contacts, such as metallized contact pads, which are arranged to receive a plurality of corresponding solder bumps or solder balls connected to the contact pads of the chip die. Further, the substrate includes circuitry on a surface thereof, including a plurality of electrical contacts such as solder pads. Each of the solder pads of the substrate and the solder bumps of the chip die are metallized so as to become solderable and electrically conductive, thus providing electrical interconnection between the a circuitry on the chip die and the circuitry on the substrate when the integrated circuit chip is mounted on the substrate. The solder bumps may be applied to the chip die in any manner as is known in the art, and may incorporate any known solder alloy, provided that such solder is reflowable. Selection of the solder alloy for the solder bumps depends, in part, on the particular melting point and on the material used for the chip and substrate.

The solder has a melting point, or more particularly, a reflow temperature, above the temperature at which the latent fluxing agent liberates the phenol or carboxylic acid, such as above about 140° C. Desirably, the solder has a melting point of between about 150° C. and 185° C.

During a microelectronic application, the fluxing underfill compositions according to the present invention may be dispensed onto the circuit board, with or without a smoothing application, and a semiconductor chip or semiconductor device positioned thereover. In particular, the inventive compositions may be applied to a circuit board having metallization pads. Solder is then disposed over the composition coated-metallization pads, and the semiconductor chip or semiconductor device may then be positioned over and mated with the circuit board, for solder reflow.

Alternatively, the solder bumps and the fluxing underfill composition may be pre-applied to the chip. In particular, the solder bumps may be applied to the electrical contacts through any known method, and the bulk underfill composition may be applied onto the chip die at a predetermined area, encompassing the solder bumps. Application of the bulk underfill composition may be accomplished using any known technique, such as a printing technique. The fluxing underfill composition may be "b-staged" after application to the chip die, such as through heating in an over at a temperature from about 40° C. to about 120° C. for a time period of about 1–6 hours, desirably at a temperature of about 80° C. to about 100° C. for a time period of about 1–3 hours. Such heating results in drying of the fluxing underfill component onto the chip die, leaving a solid residue on the chip.

After the semiconductor chip and the circuit board substrate have been mated with the fluxing underfill composition therebetween, the structure is heated to cause reflow of the solder and curing of the epoxy resin in the underfill composition. The solder reflow profile for which the inventive compositions were designed is composed of several zones, where a temperature is reached or maintained for a set time period, or temperature increases occur over a set time period. These zones may be referred to as a pre-heating zone, a soak zone and a reflow zone.

In the pre-heating zone, the circuit board and circuit chip semiconductor components are gradually heated to the soaking zone temperature. The heating gradation in the pre-heating zone may progress through the temperature range of 30° C. to 130° C. in a period of time of up to 60 seconds.

In the soaking zone, the semiconductor components are allowed to thermally equilibrate so that the thermal expansions of the semiconductor components may occur and temperature adjustments can occur. During initial heating in the soaking zone, the temperature is increased above 140° C., at which time the fluxing agent is liberated from the latent fluxing agent of the underfill composition, and removes oxides and dirt from the metallization pads and solder contacts. At such temperatures, the latent fluxing agent breaks down into substituents, in which phenol and/or a carboxylic acid are liberated. The phenol and/or carboxylic acid components act as fluxing agents and clean the metal surfaces, allowing the solder to eventually make secure electrical interconnection when exposed to elevated temperatures reached during the reflow zone. The heating gradation in the soak zone may progress through the temperature range of 150° C. to slightly greater than 180° C., such as 183° C., for a period of time of 60 to 175 seconds from initiation. In the pre-heating and soaking zones, it is desirable for the underfill composition to remain ungelled.

In the reflow zone, the solder melts, thereby flowing and forming the electrical connection. The underfill composition should gel after the solder has flowed and forms the electrical connection; otherwise, the component present can shift, thereby causing an electrical disconnect. The heating gradation in the reflow zone may progress through the temperature range of slightly greater than 180° C., such as about 183° C., to about 220° C.±10° C., for a period of time of 175 to 205–265 seconds from initiation. It is desirable for the underfill sealant to cure completely after the solder has flowed to form the electrical connection. Curing of the underfill composition establishes an electrical interconnection while encapsulating the semiconductor device onto the substrate.

As noted, the timing of this sequence is important because, should the underfill sealant begin to gel before the solder has flowed, the gelled underfill sealant will impede the ability of the solder to flow and form electrical connections. Should this occur, the microelectronic system is likely to fail, as the flow of solder aligns the semiconductor connections as well as forms the electrical connections. An underfill sealant that gels prior to the solder flowing is likely to inhibit the self alignment from occurring.

Moreover, the fluxing agents should be liberated from the composition prior to reaching the melting temperature of the solder. In particular, it is important that the fluxing agent be liberated for a sufficient time period before the solder begins to melt and reflow to make electrical connection, in order to ensure that the fluxing agent sufficiently removes any oxides and cleans the contacts.

Unlike previously developed fluxing underfill sealants, such as those described in U.S. Pat. No. 5,128,746 (Pennisi), which begin to cure in the pre-heating zone of the solder reflow profile, the inventive compositions maintain their physical properties in the uncured state through the pre-heating zone and the soak zone and only cure at the temperature reached within the solder reflow zone.

A non-limiting example of the present method for applying a chip die to a substrate is illustrated in FIGS. 1–4. In FIG. 1, a flip chip 10 containing solder bumps 12 is positioned so that the solder bumps 12 are facing a substrate 16 having an active surface 14 and aligned with the metallization pattern 18 of substrate 16. Metallization pattern 18 has a dirt and oxide layer 24. A thermally curable underfill composition with latent fluxing agent 20 is coated on the surface of substrate 16 and metallization pattern 18.

Figure 2:
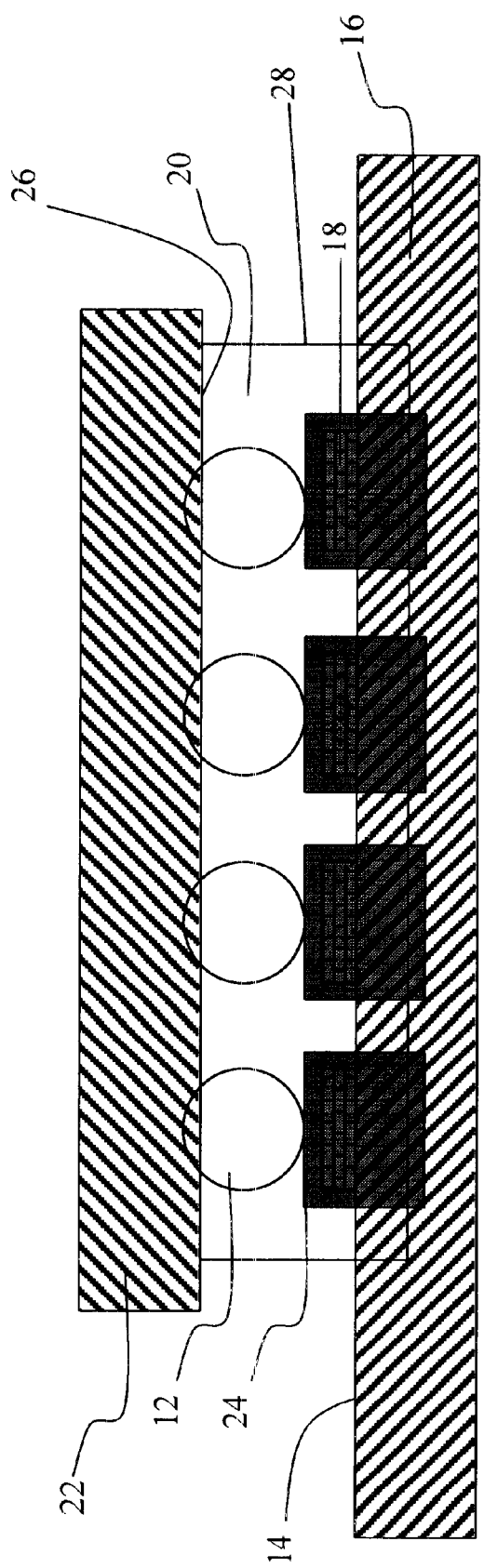
FIG. 2 depicts a cross-sectional view showing a device and substrate prior to attachment, with the two attachment surfaces to be interconnected in contact with each other.

Referring to FIG. 2, the bumped chip 22 is moved into intimate contact with metallization pattern 18 and dirt and oxide layer 24. A thermally curable underfill composition with latent fluxing agent 20 wets the bumped chip 22, insuring complete coverage of the active surface 26 of bumped chip 22. Fillet 28 provides a continuous seal around the periphery of bumped chip 22 to protect active surfaces 14 and 26 from environmental contamination.

Figure 3:
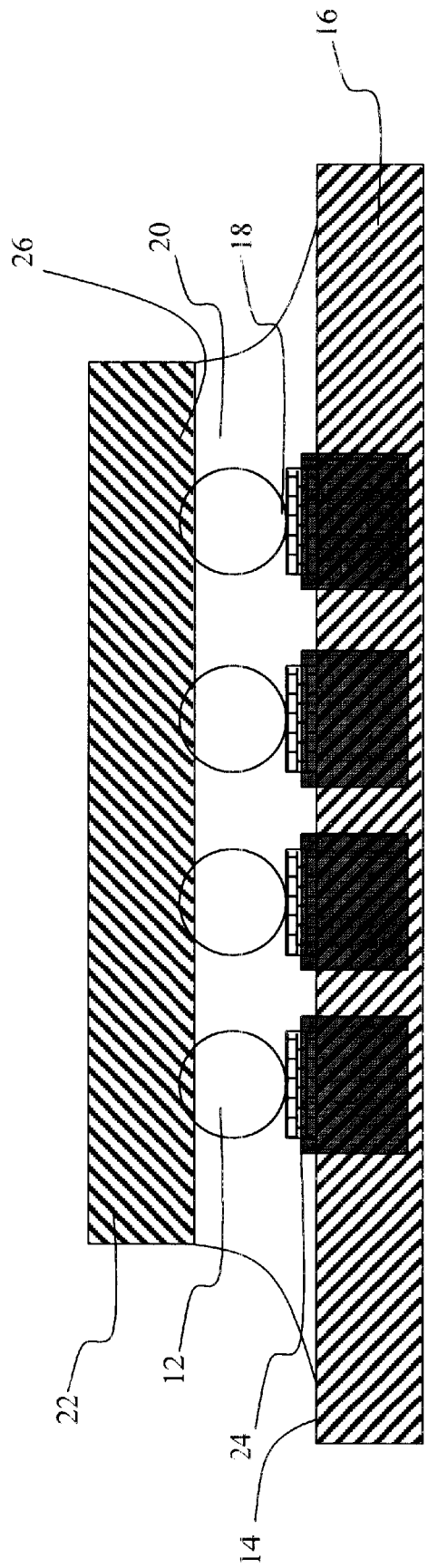
FIG. 3 depicts a cross-sectional view showing a device and substrate during initial heating, with the two attachment surfaces to be interconnected in contact with each other.

Referring to FIG. 3, when the liberating temperature of the latent flux agent of thermally curable underfill composition 20 is reached, the liberated phenol and/or carboxylic acid functional compound flux agent interacts with solder bumps 12 and metallization pattern 18, removing the majority of dirt and oxide layer 24.

Figure 4:
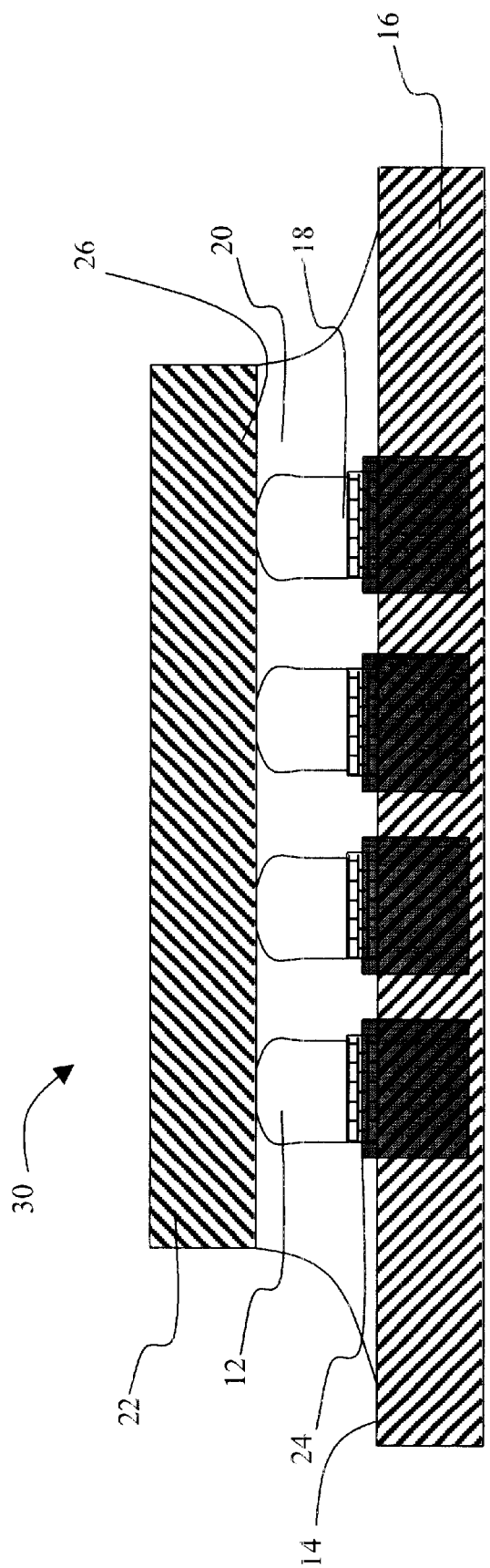
FIG. 4 depicts a cross-sectional view showing a device and substrate after bonding of the attachment surfaces.

Referring to FIG. 4, the assembly 30 is reflowed in a conventional manner such as in an oven, causing the phenol and/or carboxylic acid in the fluxing agent of the composition to become reactive, reducing the oxide layer 24 on solder bumps 12 and metallization pattern 18, and permitting alloying of the solder to the metal. After the reflow process, the fluxing agent and curable underfill composition 20 crosslink to one another, hardening the composition to a solid form.

Therefore, in the present method, exposure to a potentially corrosive environment brought on by the low pH associated with acidic fluxing agents is minimized. Further, reaction of the liberated fluxing agent in the epoxy curing process minimizes the existence of residual fluxing agents and the need to clean the integrated circuit chip produced.

The invention will be more readily understood with reference to the examples which follow, which are not to be construed so as to limit the invention.

EXAMPLES

Examples 1–5 illustrate preparation of latent fluxing agents in accordance with the present invention.

Example 1

Example 1 represents a latent fluxing agent in which the free carboxylic acid groups of a difunctional carboxylic acid are protected by reaction of the acid with a stoichiometric amount of cyclohexyl vinyl ether. A catalyst was not employed in the reaction as the product was intended for use as an additive in an epoxide adhesive where residual catalyst could compromise the stability of the formulation.

To a 250 mL reaction flask fitted with a thermocouple, magnetic stirred, pressure equalizing addition funnel and heating mantle was added 35.22 g (0.1 moles) of DIACID® 1550 (tradename of monocyclic $C_{21}$ dicarboxylic acid product derived from tall oil fatty acids and supplied by Westvaco, S.C.). The acid was stirred and heated to 77° C. and 25.24 g (0.2 moles) of cyclohexyl vinyl ether was added dropwise over 35 minutes while maintaining the temperature in the range 74–77° C. After the addition was complete, the reaction mixture was stirred for 4 hours at 77° C. and then cooled to room temperature. The reaction scheme is set forth below:

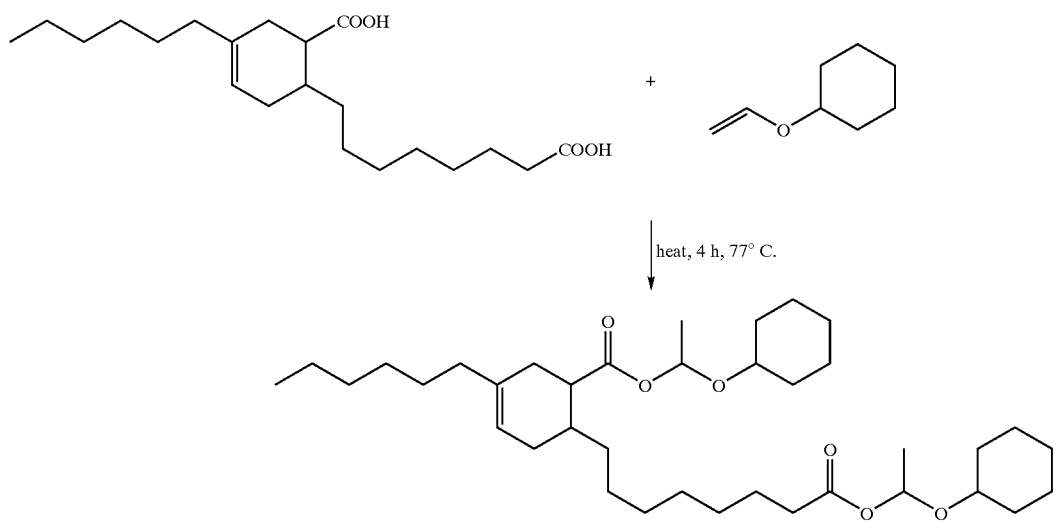

The latent acid product was obtained as a yellow colored oil (58.57 g, 97% yield) and used without further purification.

Figure 5:
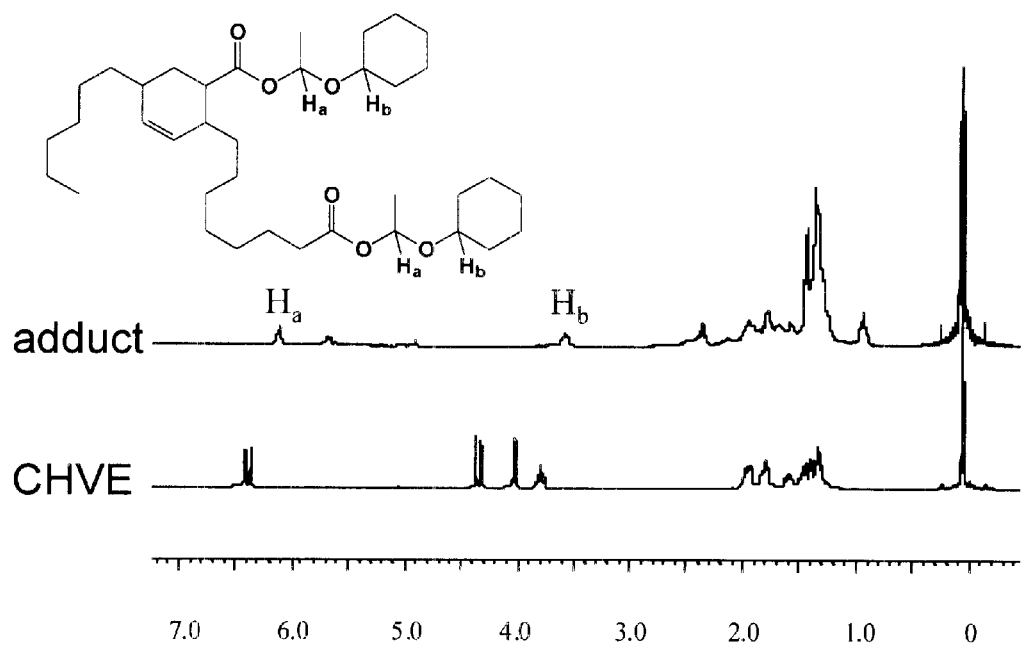
FIG. 5 depicts a $^1$H NMR spectrum of the adduct produced in accordance with Example 1.

The structure of the product was shown by $^1$H NMR and IR analyses to be bis-(1-clohexyloxyethyl) ester of the starting DIACID®. The $^1$H NMR spectrum of the adduct along with the key proton assignments is shown in FIG. 5. The α-acetal and α-ether protons of the adduct at δ 6.1 and 3.6 are clearly distinguishable. For comparative purposes the spectrum of the starting vinyl ether is also shown. It is clear from the spectra that there is no residual vinyl ether in the crude adduct (i.e. the vinyl protons of the starting vinyl ether at δ 4.1, 4.5 and 6.4 are not observed in the spectrum of the adduct).

Figure 6:
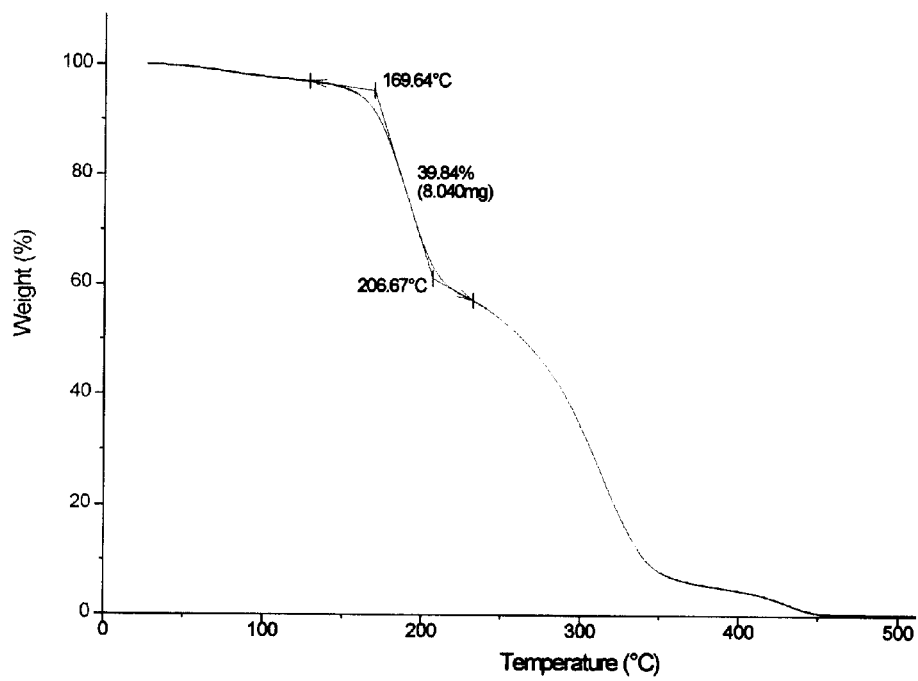
FIG. 6 depicts a thermogravimetric analysis profile of the adduct produced in accordance with Example 1.

Thermolysis of the adduct was investigated by dynamic thermogravimetric analysis ("TGA") at a heating rate of 10° C./minute. The TGA profile, shown in FIG. 6, indicates that weight loss occurs in two distinct stages as the temperature increases. The first onset occurs at 170° C. and accounts for about 40% of the sample weight. This is followed by a second degradation at about 250° C. This behavior indicates that adduct undergoes a thermal reversion reaction at a temperature below 170° C. followed by the loss of the volatile vinyl ether constituent. The observed weight loss of about 40% corresponds closely to the expected loss of 42%, which is calculated from the structure of the adduct. The second stage of weight loss corresponds to the decomposition of the diacid fragment. The thermolysis of the adduct is shown schematically below:

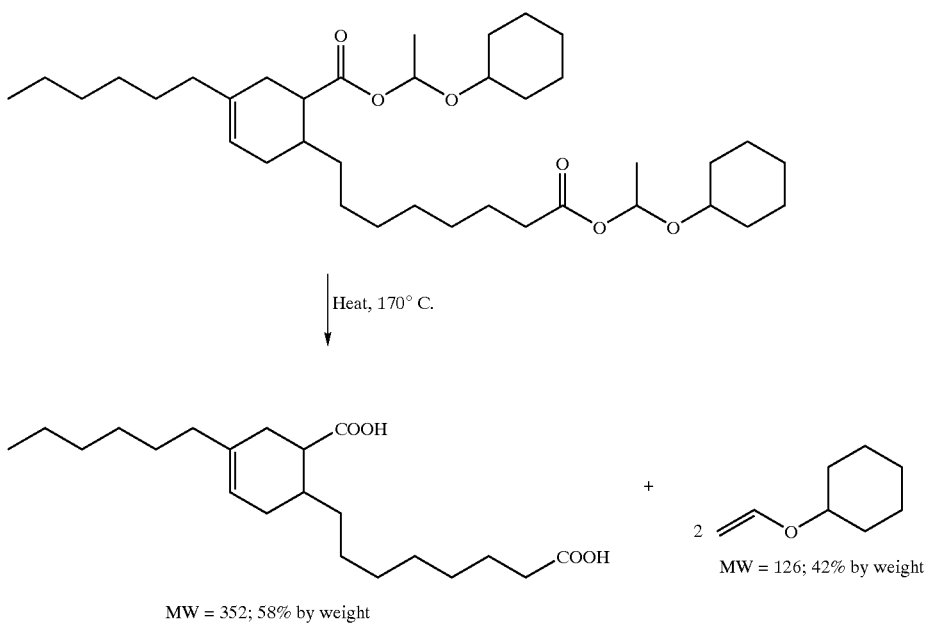

Thermolysis of DIACID® 1550/CHVE Adduct

Example 2

The corresponding adduct of DIACID® 1550 and 2-ethylhexyl vinyl ether was synthesized by a similar procedure to that described in Example 1. After stirring for 4.5 hours at 110° C., the product was obtained in 95% yield. The structure was confirmed by spectroscopic analysis. The reaction scheme is outlined below:

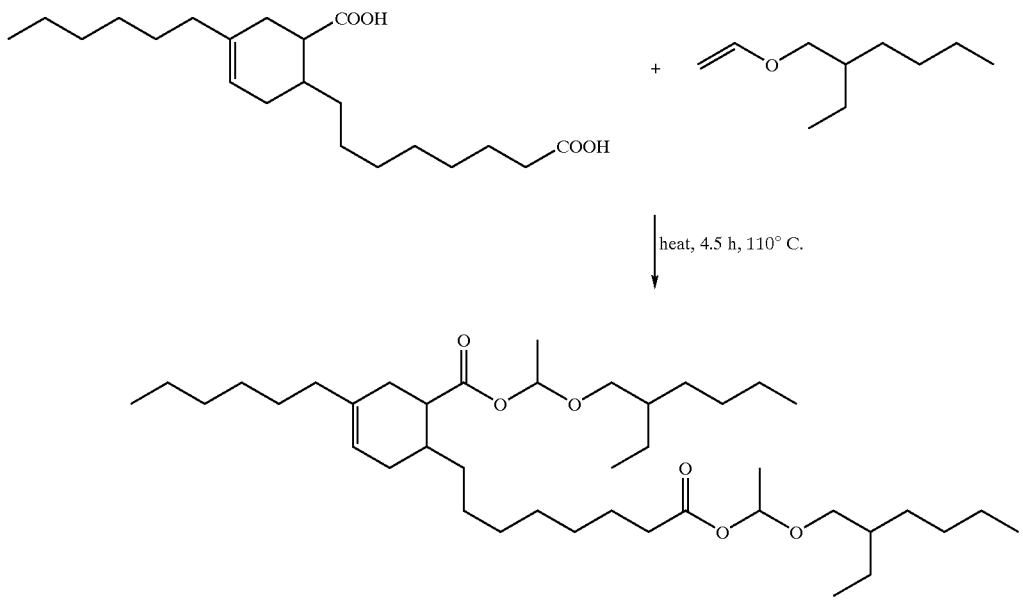

Synthesis of DIACID® 1550/2-Ethylhexyl Vinyl Ether Adduct

Figure 7:
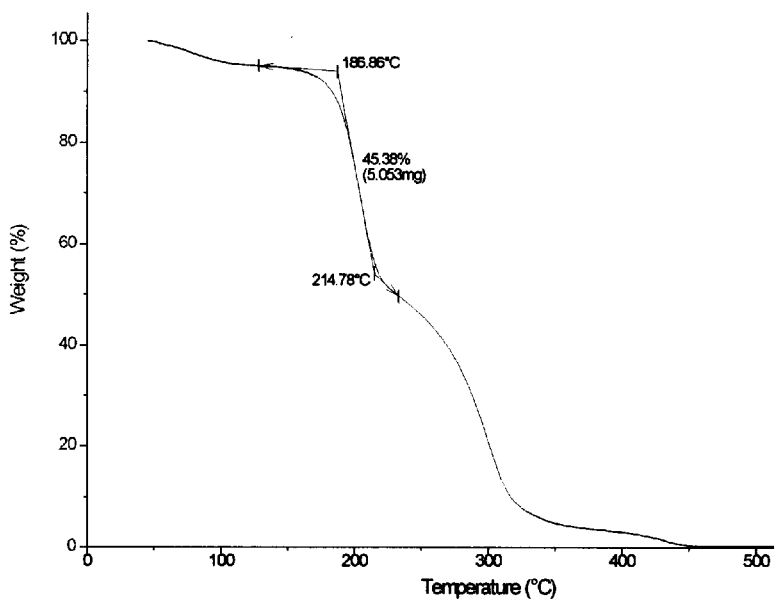
FIG. 7 depicts a thermogravimetric analysis profile of the adduct produced in accordance with Example 2.

Thermolysis of the product was examined by TGA. Initial weight loss of 50% was observed. This amount corresponds closely to the theoretical value of 49%, which would be expected from the loss of 2-ethylhexyl vinyl ether following the decomposition of the adduct. The onset of weight loss was observed at 187° C. This value is 17° C. higher than that observed for the decomposition of the adduct of Example 1 and is attributed to the lower volatility of 2-ethylhexyl vinyl ether (b.p. 178° C.) compared to cyclohexyl vinyl ether (b.p. 151° C.). The TGA profile is shown in FIG. 7.

Example 3

The adduct of 0.1 moles DIACID® 1550 and 0.2 moles of (4-vinyloxy)butyl benzoate was synthesized by a procedure similar to that described in Example 1. After stirring for 6 hours at 110° C., the product was obtained in 96% yield. The structure was confirmed by spectroscopic analysis. The reaction scheme is outlined below:

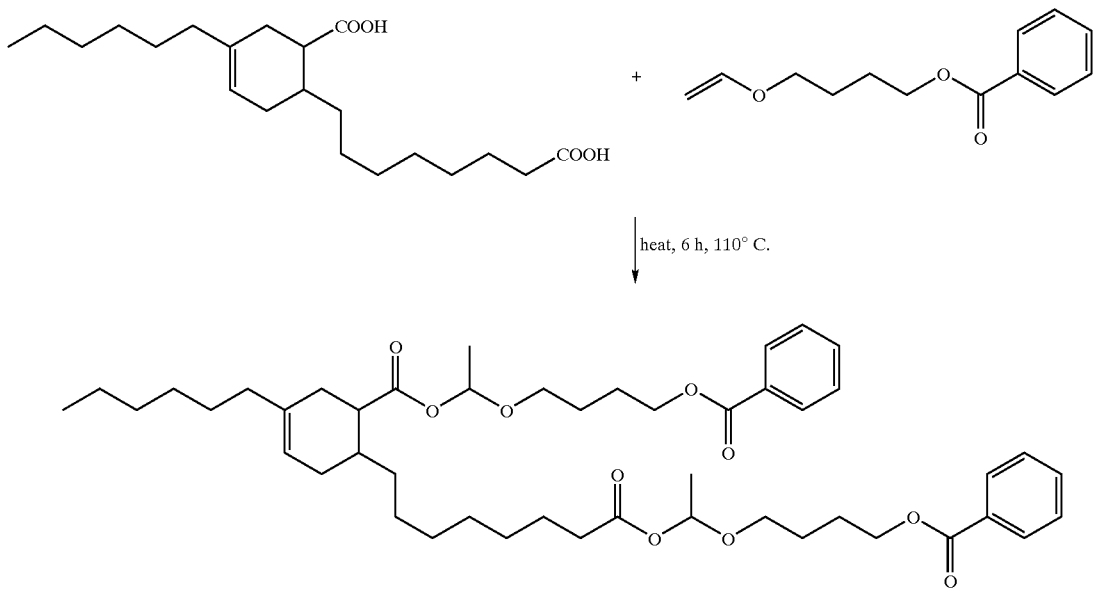

Synthesis of DIACID® 1550/(4-Vinyloxy)butyl Benzoate Adduct

Figure 8:
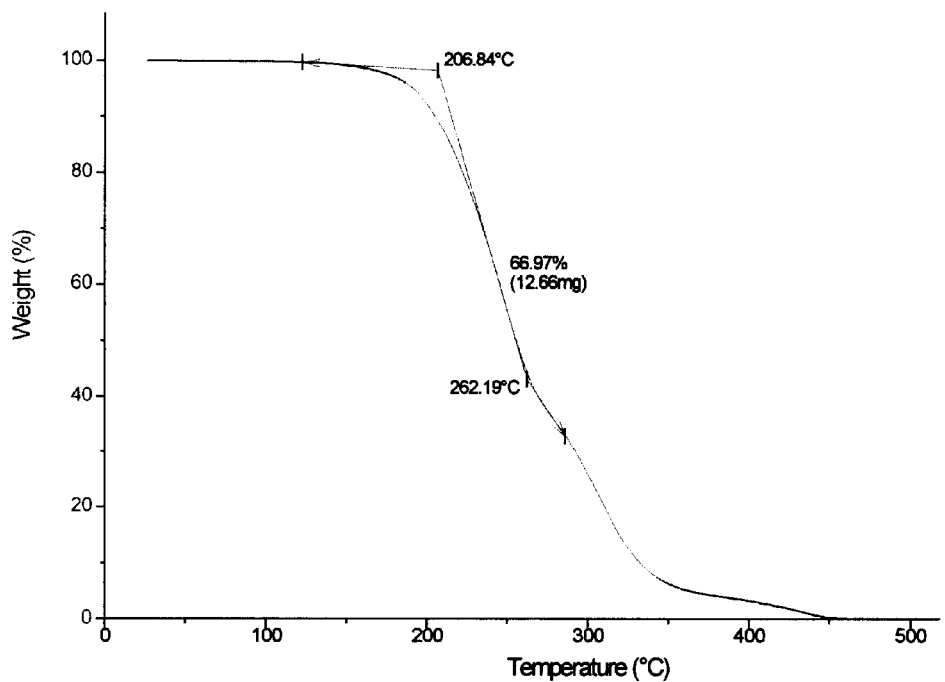
FIG. 8 depicts a thermogravimetric analysis profile of the adduct produced in accordance with Example 3.

Thermolysis of the product was examined by TGA. Initial weight loss of about 60% was observed. This amount corresponds closely to the theoretical value of 56%, which would be expected from the loss of (4-vinyloxy)butyl benzoate following the decomposition of the adduct. The onset of weight loss was observed at 207° C. This value is 37° C. higher than that observed for the decomposition of the adduct of example 1 and may be attributed to the lower volatility of (4-vinyloxy)butyl benzoate (b.p. 304° C.) compared to cyclohexyl vinyl ether (b.p. 151° C.). The TGA profile is shown in FIG. 8.

Example 4

The adduct of 0.1 moles DIACID® 1550 and 0.2 moles of (4-(1-propenyloxymethyl)-1,3-dioxolan-2-one (propylene ether of propylene carbonate) was synthesized by a procedure similar to that described in Example 1. After stirring for 30 hours at 110° C., the product was obtained in 86% yield. The structure was confirmed by spectroscopic analysis. The reaction scheme is outlined below:

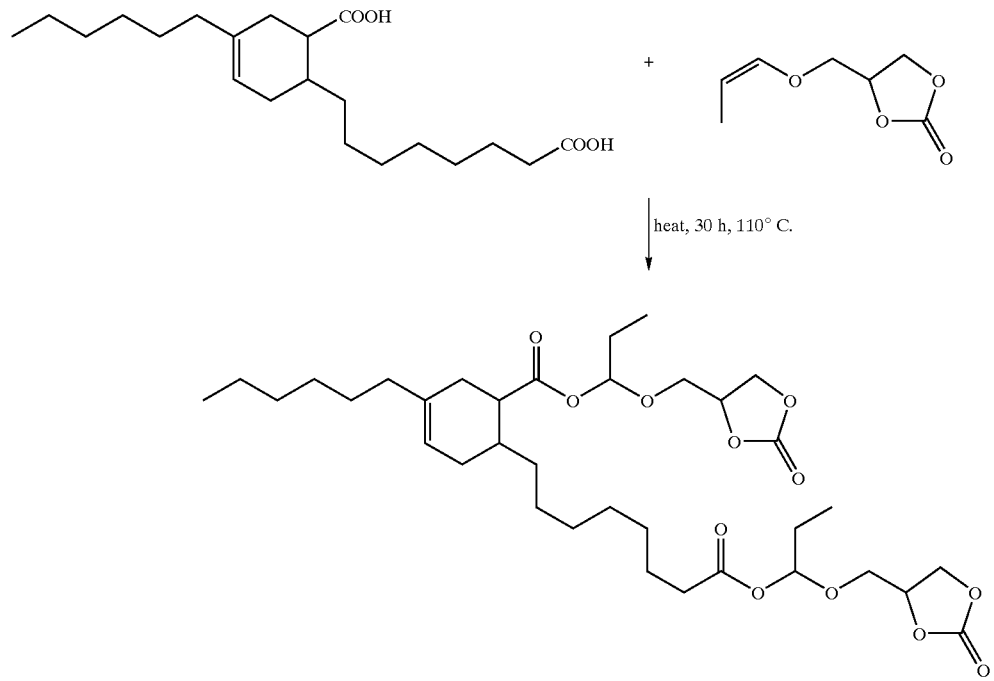

Synthesis of DIACID® 1550/4-(1-Propenyloxymethyl)-1,3-dioxolan-2-one Adduct

Figure 9:
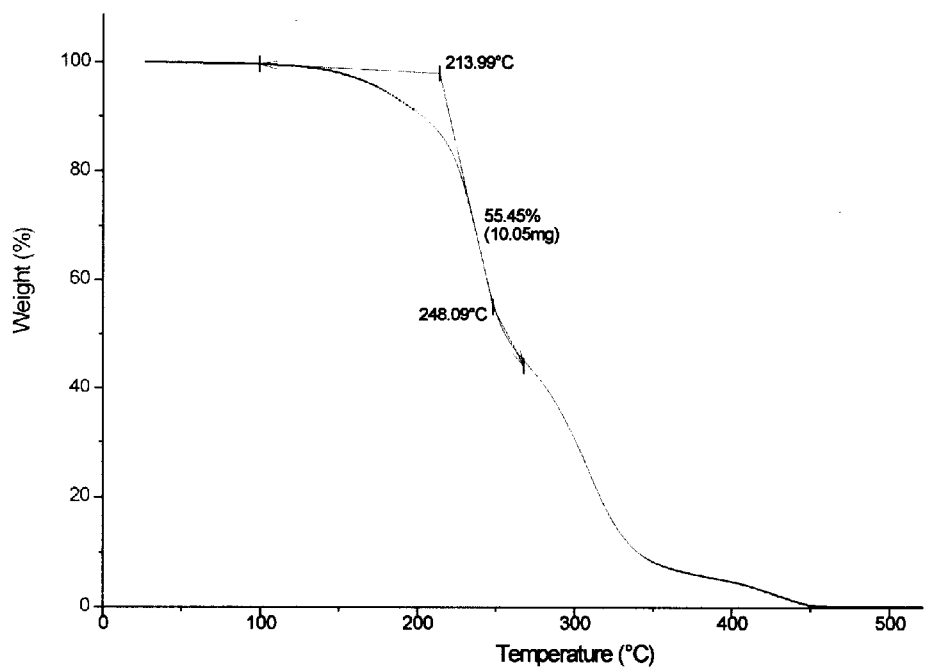
FIG. 9 depicts a thermogravimetric analysis profile of the adduct produced in accordance with Example 4.

Thermolysis of the product was examined by TGA. The onset of weight loss was observed at 214° C. and an initial weight loss of about 50% was observed. This amount corresponds closely to the theoretical value of 47%, which would be expected from the loss of 4-(1-propenyloxymethyl)-1,3-dioxolan-2-one following the decomposition of the adduct. The TGA profile is shown in FIG. 9.

Example 5

A polymeric vinyl ether terminated α-alkoxy ester was synthesized by the reaction of excess divinyl ether, 1,4-bis(vinyloxy)methylcyclohexane, with DIACID® 1550. The procedure used was as follows. To a 25 mL reaction flask equipped with a magnetic stirrer and heating bath was added 3.14 g (8.5 millimoles) of DIACID® 1550 and 1.96 g (10 millimoles) of 1,4-bis(vinyloxy)methylcyclohexane. The mixture was stirred and heated at 85° C. for 5 hours and cooled, with the reaction scheme outlined below:

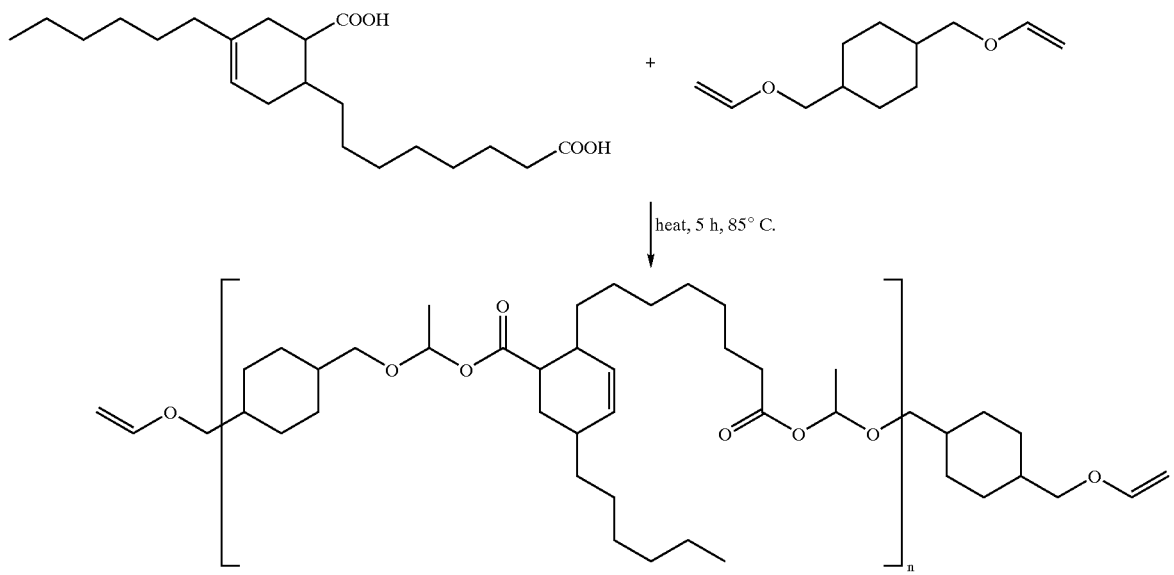

The resultant product was obtained as a yellow colored tacky solid (5.10 g, 100%) yield) and shown by $^1$H NMR and IR analyses to be the vinyl ether terminated polymer having a number average degree of polymerization (n) of about 8. The polymer is soluble in common epoxy monomers and is particularly useful for providing latent fluxing underfill adhesives with high viscosity. The molecular weight and viscosity of the polymer may be increased by reducing the amount of excess vinyl ether employed. If a stoichiometric deficiency of vinyl ether is used, the corresponding carboxylic acid functionalized polymer is obtained.

Example 6

Example 6 demonstrates the synthesis of bis-1-(1',6'-hexoxy)ethyl-3,4-epoxycyclohexane carboxylate (2) ("BHEC") from commercially available reagents, for use as a latent fluxing agent. The reaction scheme is illustrated below and employs a divinyl ether having epoxy functionality and a mono-alkenyl carboxylic acid:

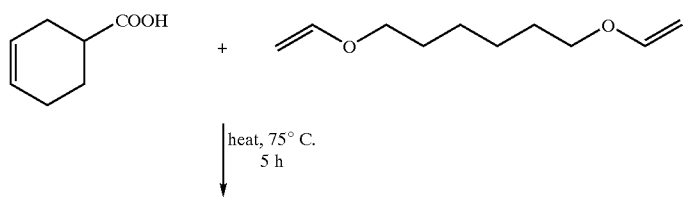

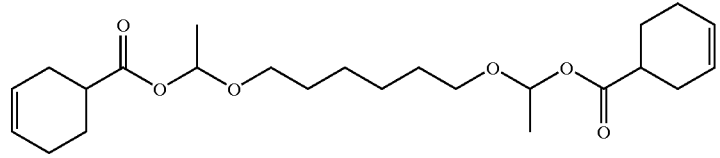

(1; intermediate)

CPB; 5° C.
20 h

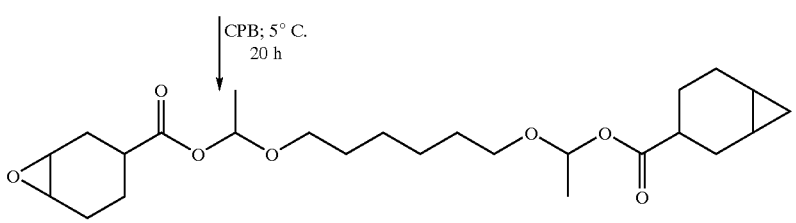

(2; BHEC)

1,6-Hexanediol divinylether (17.0 g; 0.05 moles) was added to a 50 mL reaction flask fitted with a thermocouple, magnetic stirrer, addition funnel and heating mantle. The monomer was heated to 75° C. and 3-cyclohexene-1-carboxylic acid (25.2 g; 0.1 moles) was added dropwise over 25 minutes while the temperature was maintained between 75–78° C. After the addition was complete, the stirred mixture was heated for an additional 5 hours and cooled. The crude liquid was vacuum filtered through a short column of basic aluminum to give the intermediate product bis-1-(1', 6'-hexoxy)ethyl cyclohex-3-enecarboxylate (1) (31.968 g; 76% yield). The structure of the product was confirmed by $^1$H NMR and IR spectral analyses.

The intermediate product (1) (8.44 g; 0.02 moles) was dissolved in dichloromethane (30 mL) and the resultant solution added dropwise over 45 minutes to a stirred solution of 3-chloroperoxybenzoic acid (10.62 g of 65% pure grade; 0.04 moles) in dichloromethane (50 mL). The addition was performed in a 250-mL reactor fitted with a thermocouple, addition funnel, magnetic stirrer and ice bath. The temperature was maintained between 2 and 7° C. throughout the addition. The mixture was stirred for a further 20 hours during which time the temperature was allowed to slowly increase to the ambient value. The reaction mixture was filtered to remove solids, which were rinsed with dichloromethane (20 mL) and the combined filtrate and rinsings washed with 10% sodium sulfite solution (2×50 mL portions), saturated sodium bicarbonate solution (3×50 mL portions) and deionized water (3×50 mL portions). The washed solution was dried over anhydrous sodium sulfate, filtered and the solvent removed under reduced pressure to yield of BHEC monomer (2) (7.76 g; 86% yield). The structure of the product was confirmed by $^1$H NMR and IR spectral analyses. The reaction may be conducted in the absence of an acidic catalyst.

Example 7

Example 7 demonstrates the synthesis of bis-3,4-epoxycyclohexane carboxylate of 1,4-cyclohexane dimethanol divinyl ether ("ECCD"), for use as a latent fluxing agent.

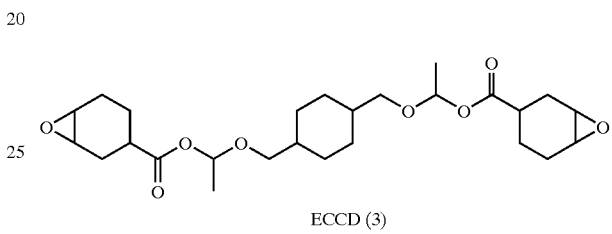

ECCD (3)

The reaction involves commercially available starting materials of a divinyl ether having epoxy functionality and a mono-alkenyl carboxylic acid. The bis-epoxide monomer ECCD (3) shown above was prepared for use as a latent fluxing agent in a manner analogous to that described in Example 7. Initially a mixture of 1,4-cyclohexane dimethanol divinyl ether (35.00 g; 0.18 moles) and 3-cyclohexene-1-carboxylic acid (45.00 g; 0.36 moles) was heated at 75–100° C. for 3 hours to prepare the intermediate di-unsaturated α-alkoxyester (100% yield). The intermediate was then epoxidized with 3-chloroperoxybenzoic acid at 0–3° C. according to the process described in Example 7. The product was isolated in 91% yield. The structures of the intermediate and final product were confirmed by $^1$H NMR and IR spectral analyses.

Example 8

Example 8 demonstrates the synthesis of tris-3,4-epoxycyclohexane carboxylate of trimethylolpropane trivinyl ether ("ECCT") (4), for use as a latent fluxing agent.

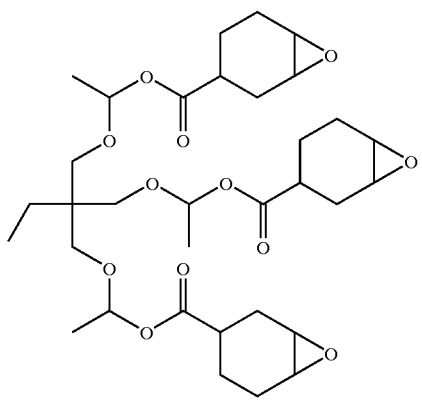

ECCT (4)

This example describes a method used to prepare an inventive fluxing agent from a commercially available trivinyl ether having epoxy functionality and a commercially available mono-alkenyl carboxylic acid. A similar reaction scheme to that shown in Example 7 was used to make the epoxy monomer of the present example, i.e. ECCT (4).

Trimethylolpropane trivinylether (35.4 g; 0.167 moles) was added to a 250-mL reaction flask fitted with a thermocouple, magnetic stirrer, addition funnel and heating mantle. The monomer was heated to 70° C. and 3-cyclohexene-1-carboxylic acid (63.0 g; 0.5 moles) was added dropwise at such a rate as to maintain the temperature between 73–75° C. After the addition was complete, the stirred mixture was heated for an additional 7 hours and cooled. The crude product was dissolved in dichloromethane (100 mL) and the solution passed through a short column of basic alumina. The solvent was then removed by distillation under reduced pressure to give the desired tri-unsaturated α-alkoxyester intermediate (83.0 g; 84% yield). The structure of the product was confirmed by $^1$H NMR and IR spectral analyses.

To a 1-L reactor fitted with a thermocouple, addition funnel, magnetic stirrer and ice bath was added 3-chloroperoxybenzoic acid (112.07 g of 65% pure grade; 0.42 moles) and dichloromethane (350 mL). The mixture was stirred to dissolve the acid and cooled to about 1° C. The tri-functional intermediate product (83.0 g; 0.14 moles) was dissolved in dichloromethane (250 mL) and the resultant solution added dropwise to the reaction mixture at such a rate as to maintained the temperature in the range 1–3° C. (about 2 hours). After the addition was complete the mixture was stirred for a further 2 hours at 1–3° C., filtered and the filtrate washed with 10% sodium sulfite solution (2×400 mL portions), saturated sodium bicarbonate solution (2×400 mL portions) and deionized water (2×500 mL portions). The washed solution was dried over anhydrous sodium sulfate, filtered and the solvent removed under reduced pressure to yield of ECCT monomer (4) (72.0 g; 80% yield) as a viscous oil. The structure of the product was confirmed by $^1$H NMR and IR spectral analyses.

Example 9

This example describes a method for preparing 1-propenyl glycidyl ether ("PGE"), a 1-alkenyl ether from readily available and inexpensive reagents. The reaction scheme is illustrated below. Once formed, this compound becomes a useful reactant to make the latent fluxing agents having epoxy functional end groups in accordance with one embodiment of the present invention.

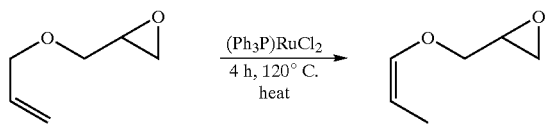

To a 1-liter reaction flask equipped with a magnetic stirrer, condenser, thermocouple, nitrogen inlet and heating mantel was added allyl glycidyl ether (342 g; 3.0 moles) and tris(triphenylphosphonium)ruthenium (II) chloride (5.23 g; 5.45 millimoles). The mixture developed a brown color as the catalyst was dissolved. The solution was stirred and heated to 120° C. under a nitrogen atmosphere. After 4 hours, the reaction mixture was cooled to room temperature and distilled under vacuum to give the isomerized product, 1-propenyl glycidyl ether as a colorless liquid, b.p. 58–62° C. at 20 torr (304 g, 89% yield). The structure of the product was confirmed by $^1$H NMR and IR spectral analyses and found to be a 3:2 blend of Z:E isomeric forms.

PGE monomer has two different reactive functional groups, viz. an epoxide and a 1-propenyl ether. It has been discovered that PGE may be reacted with carboxylic acids exclusively through the propenyl ether group when there is at least one equivalent of propenyl ether per equivalent of carboxylic acid present in the reaction mixture. The reaction may be conducted neat (without added solvent) and in the absence of an acidic catalyst, which is typically employed in the syntheses of conventional α-alkoxy esters.

Example 10

This example describes a method for preparing bis-(α-glycidoxypropyl) glutarate ("BGPG"), a curable epoxidized compound useful as a latent fluxing agent according to the present invention, through reaction products of PGE prepared in Example 9 and a commercially available polycarboxylic acid, glutaric acid. The reaction scheme is illustrated below.

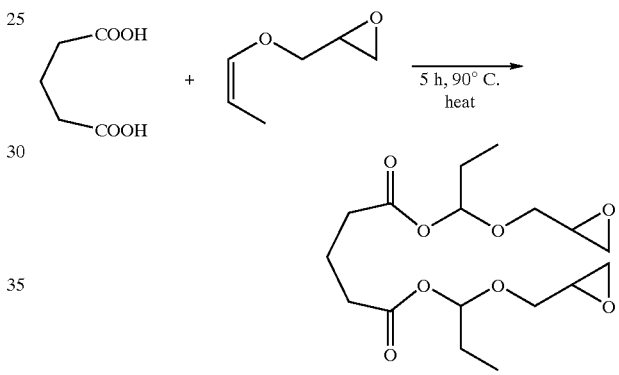

To a 250 ml reaction flask equipped with a magnetic stirrer heating mantel and thermocouple was added PGE (50.0 g, 0.439 moles) and glutaric acid (24.6 g, 0.187 moles). The mixture was heated to 90° C., during which time the acid dissolved in the PGE. Heating and stirring were continued for 5 hours. The reaction mixture was cooled to room temperature, dissolved in acetone (200 mL) and filtered through a short column of basic alumina to remove traces of unreacted acid. The solvent and excess PGE were removed by distillation under reduced pressure to give the bis-(α-glycidoxypropyl) glutarate (BOPG) (38.1 g; 57% yield) as a colorless liquid. The structure of the product was confirmed by $^1$H NMR and IR analyses.

Example 11

This example describes the process of preparing bis-(α-glycidoxypropyl) pimelate ("BGPP") as a fluxing agent in accordance with the present invention. The reaction scheme is illustrated below.

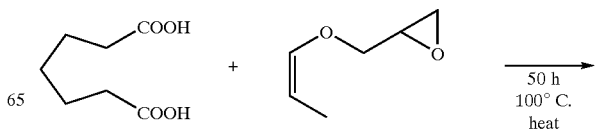

-continued

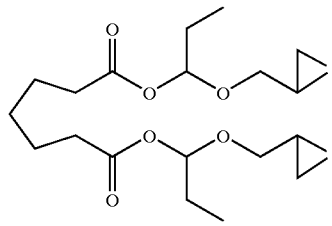

To a 250 ml reaction flask equipped with a magnetic stirrer, heating mantel and thermocouple was added PGE (66.3 g, 0.58 moles) and pimelic acid (40.0 g, 0.25 moles). The mixture was heated and stirred at 100° C. for 50 hours. After cooling to 65° C., the reaction flask was connected to a vacuum pump and excess PGE was removed over 3 hours at a pressure of 350 mtorr. Bis-(α-glycidoxypropyl) pimelate ("BGPP") was isolated in quantitative yield as a viscous oil. The structure of the product was confirmed by $^1$H NMR and IR analyses.

Example 12

Two underfill compositions were prepared as Composition A and Composition B. Composition A represents a conventional fluxing underfill composition, which includes an epoxy resin composition and a carboxylic acid as a fluxing agent within the resin composition. Composition B, on the other hand, represents a fluxing underfill composition according to the present invention, which includes an epoxy resin composition and an epoxy-terminated alkoxy ester as a latent fluxing agent within the resin composition. The compositions were prepared having the following ingredients identified below:

TABLE 1

| Ingredient | Composition A (weight percent) | Composition B (weight percent) |
|---|---|---|
| Bisphenol A epichlorohydrin copolymer[1] | 4 | 4 |
| Liquid bisphenol A epoxy resin[2] | 26 | 26 |
| Carboxylic acid[3] | 9 | — |
| α-alkoxy ester[4] | — | 16.2 |
| Curing agent complex[5] | 0.6 | 0.6 |
| Silane adhesion promoter[6] | 0.6 | 0.6 |
| Air release agent[7] | 0.1 | 0.1 |
| Anhydride[8] | 24 | 24 |

[1]EPON 1002f, commercially available from Shell Chemical Co.
[2]RE 310 S, commercially available from Nippon Kayaku, Japan
[3]DIACID ® 1550, a monocyclic C-21 dicarboxylic acid, commercially available from Westvaco Corporation
[4]prepared from a reaction mixture of DIACID ® 1550 and 2-vinyloxyethyl glycidyl ether
[5]1:1 complex of DBU/DIACID ® 1550
[6]OSI A187, glycidoxypropyl trimethoxysilane, commercially available from OSI.
[7]BYK-555, commercially available from BYK-Chemie.
[8]LINDRIDE 62C, commercially available from Lindau Chemicals, Inc.

Two microelectronic assemblies were prepared with a 10 FB250 chip die on a circuit board substrate, with the first assembly using Composition A as an underfill material and the second assembly using Composition B as an underfill material. Both of the assemblies were reflowed using a standard eutectic reflow profile, in which the assemblies are heated rapidly to a temperature between 150° and 185° C. and then held at this temperature for approximately 1 minute (the soaking zone). After the soak, the temperature is raised to 220–265° C. for solder reflow (the reflow zone). Following reflow, the parts are cooled to room temperature by a cooling zone. Percent yield of the resin compound was measured after reflow. Composition A demonstrated a yield of 30 percent, while Composition B demonstrated a yield of 50 percent. Such an improvement in yield as seen through the inventive composition including the latent fluxing agent is believed to be due to the masking aspect of the latent fluxing agent, such that the fluxing agent is prevented from undesirably causing degradation of the epoxy resin prior to curing thereof. Moreover, similar solder wetting was observed with both assemblies, indicating that the latent fluxing agent of Composition B provides proper fluxing activity for the contacts.

What is claimed is:

1. A method for bonding a chip die, which has one or more solderable contacts, to a substrate comprising:
   (a) placing the chip die in contact with the substrate;
   (b) providing an underfill composition between the chip die and the substrate, the underfill composition comprising:
      (i) an epoxy resin,
      (ii) a latent fluxing agent which liberates a phenolic compound or a carboxylic acid-containing compound when heated above 140° C., and
      (iii) a compound for effecting cure of the epoxy resin; and
   (c) applying a temperature greater than 140° C. to the substrate with the chip die and underfill composition, such that a phenolic compound or a carboxylic acid-containing compound is released, and reflow of the solderable contacts and curing of the underfill composition occur.

2. The method of claim 1, wherein the underfill composition is provided on the chip die prior to the step of placing the chip die in contact with the substrate.

3. The method of claim 1, wherein in the underfill composition, the latent fluxing agent in (ii) is selected from the group consisting of an α-alkoxyalkyl ester of a carboxyl-containing compound and an α-alkoxyalkyl phenyl ether.

4. The method of claim 1, wherein the temperature applied in (c) is applied using a solder reflow oven.

5. The method of claim 1, wherein the substrate is selected from the group consisting of $Al_2O_3$, $SiN_3$, mullite ($Al_2O_3$—$SiO_2$), polyimide, glass-reinforced epoxy, acrylonitrile-butadiene-styrene and phenolic substrates.

6. The method of claim 1, wherein the chip die is a flip chip.

7. An integrated circuit chip prepared using the method of claim 1.

* * * * *

UNITED STATES PATENT AND TRADEMARK OFFICE
CERTIFICATE OF CORRECTION

PATENT NO.    : 6,667,194 B1
DATED         : December 23, 2003
INVENTOR(S)   : Lawrence N. Crane et al.

It is certified that error appears in the above-identified patent and that said Letters Patent is hereby corrected as shown below:

Column 8,
Lines 3-9, replace the figure with the following: 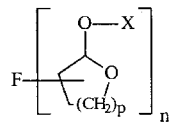

Column 10,
Line 59, change "dihydroflumaric" to -- dihydrofumaric --

Column 31,
Line 30, change "maintained" to -- maintain --

Column 32,
Line 11, change "neat" to -- neatly --

Signed and Sealed this

Seventh Day of September, 2004

JON W. DUDAS
*Director of the United States Patent and Trademark Office*